US006770279B1

(12) United States Patent
Feldmann et al.

(10) Patent No.: US 6,770,279 B1
(45) Date of Patent: Aug. 3, 2004

(54) TNFα ANTAGONISTS AND CYCLOSPORIN IN THERAPY OF RHEUMATOID ARTHRITIS

(75) Inventors: Marc Feldmann, London (GB); Ravinder N. Maini, London (GB); Richard O. Williams, London (GB)

(73) Assignee: The Kennedy Institute of Rheumatology, London (GB)

( * ) Notice: Subject to any disclaimer, the term of this patent is extended or adjusted under 35 U.S.C. 154(b) by 0 days.

(21) Appl. No.: 09/093,450

(22) Filed: Jun. 8, 1998

Related U.S. Application Data

(63) Continuation of application No. 08/607,419, filed on Feb. 28, 1996, now abandoned, which is a continuation-in-part of application No. 08/403,785, filed on May 3, 1995, now Pat. No. 5,741,488, which is a continuation-in-part of application No. PCT/GB94/00462, filed on Mar. 10, 1994, which is a continuation-in-part of application No. 07/958,248, filed on Oct. 8, 1992, now abandoned.

(51) Int. Cl.$^7$ .................. A61K 39/395; A61K 38/00
(52) U.S. Cl. ................ 424/145.1; 424/130.1; 424/141.1; 424/152.1; 424/158.1; 514/9; 514/11
(58) Field of Search ............... 424/130.1, 141.1, 424/144.1, 154.1, 173.1; 514/11, 9

(56) References Cited

U.S. PATENT DOCUMENTS

| | | | |
|---|---|---|---|
| 4,695,459 A | 9/1987 | Steinman et al. ............. 424/95 |
| 5,204,329 A | * 4/1993 | Ackerman et al. | |
| 5,317,019 A | 5/1994 | Bender et al. ............ 514/224.2 |
| 5,502,066 A | 3/1996 | Heinemann et al. ........ 514/360 |
| 5,580,873 A | 12/1996 | Bianco et al. ............. 514/263 |
| 5,656,272 A | 8/1997 | Le et al. .................. 424/133.1 |
| 5,672,347 A | 9/1997 | Aggarwal et al. ....... 424/139.1 |
| 5,698,195 A | 12/1997 | Le et al. | |
| 5,795,967 A | 8/1998 | Aggarwal et al. | |
| 5,919,452 A | 7/1999 | Le et al. | |
| 5,994,510 A | 11/1999 | Adair et al. | |

FOREIGN PATENT DOCUMENTS

| | | |
|---|---|---|
| WO | WO 89/08460 | 9/1989 |
| WO | WO 92/07585 | 5/1992 |
| WO | WO 92/08474 | 5/1992 |
| WO | WO 98/24463 | 6/1998 |

OTHER PUBLICATIONS

Horneff, G., et al., "Elevated levels of circulating tumor necrosis factor–α, interferon–γ, and interleukin–2 in systemic reactions induced by anti–CD4 therapy in patients with rheumatoid arthritis", *Cytokine*, 3(3):266–247 (1991).

Brennan, F., et al., "Inhibitory effect of TNFα antibodies on synovial cell interleukin–1 production in rheumatoid arthritis", *The Lancet*, 2(8657):244–247 (1989).

Steinbruchel, D., et al., "Monoclonal antibody treatment (anti–CD4 and anti–interleukin–2 receptor) combined with cyclosporin A has a positive but not simple dose–dependent effect on rat renal allograft survival", *Scandinavian J. Immunol.*, 34(5):627–633 (1991).

Breedveld, F., et al., "Anti–CD4 antibodies in rheumatoid arthritis", *Clin. Experimental Rheum.*, 10(4):325–326 (1992).

Brennan, F., et al., TNFα—a pivotal role in rheumatoid arthritis?, *British J. Rheumatology*, 31(5):293–298 (1992).

Elliott, M.J., et al., "Treatment of rheumatoid arthritis with chimeric monoclonal antibodies to TNF–α: safety, clinical efficacy and control of the acute phase response", *Cell. Biochemistry, Supplement*, 0(17B):145 (1993); Abstract EZ405.

Williams, R.O., et al., "Synergy between anti–CD4 and anti–tumor necrosis factor in the amelioration of established collagen–induced arthritis", *Proc. Natl. Acad. Sci. USA*, 91:2762–2766 (1994).

Ralph, P., "Clinical and Preclinical Studies Presented at the Keystone Symposium on Arthritis, Related Diseases, and Cytokines," *Lymphokine Cytokine Research.*, 12(4):261–263 (1993).

Racadot, E., "Immunological follow–up of 17 patients with rheumatoid arthritis treated in vivo with an anti–T CD4+ monoclonal antibody (B–F5)," *Clinical Experimental Rheumatology*, 10:365–374 (1992).

Williams, R.O., et al., "Successful therapy of collagen–induced arthritis with TNF receptor–IgG fusion protein and combination with anti–CD4," *Immunology*, 84:433–439 (Mar. 1995).

Van Der Lubbe, P.A., et al., "A Randomized, Double–Blind, Placebo–Controlled Study of CD4 Monoclonal Antibody Therapy In Early Rheumatoid Arthritis," *Arth. Rheuma.*, 38(8):1097–1106 (1995).

Choy, E.H.S., et al., "Therapeutic Monoclonal Antibodies," *British J. Rheumatology*, 34:707–715 (1995).

Rankin, E.C.C., et al., "The Therapeutic Effects of an Engineered Human Anti–Tumour Necrosis Factor Alpha Antibody (CDP571) in Rheumatoid Arthritis," *British J. Rheumatology*, 34: 334–342 (1995).

Butler, D.M., et al., "Modulation of proinflammatory cytokine release in rheumatoid synovial membrane cell cultures. Comparison of monoclonal anti TNF–α antibody with the interleukin–1 receptor antagonist," *Eur. Cytokine Netw.*, 6(4): 225–230 (1995).

(List continued on next page.)

*Primary Examiner*—Phillip Gambel
(74) *Attorney, Agent, or Firm*—John P. White; Cooper & Dunham LLP

(57) ABSTRACT

A method for treating rheumatoid arthritis using a TNFα antagonist in combination with cyclosporin or analog thereof is disclosed.

2 Claims, 11 Drawing Sheets

OTHER PUBLICATIONS

Horneff, G., et al., "Treatment of Rheumatoid Arthritis with an Anti–CD4 Monoclonal Antibody," *Arth. Rheumatism*, *34*(2): 129–140 (1991).

Van Dullemen, H.M., et al., "Treatment of Crohn's Disease With Anti–Tumor Necrosis Factor Chimeric Monoclonal Antibody (cA2)," *Gastroenterology*, *109*(1):129–135 (1995).

Watts, R.A., and Isaacs, J.D., "Immunotherapy of rheumatoid arthritis," *Annals Rheumatic Diseases, 51*:577–579 (1992).

Schacht, E., Gegenwärtige und zukünftige Therapiestrategien der rheumatoiden Arthritis (RA)*) [The current and future therapy strategies of rheumatoid arthritis (RA)], *Zeitschrift für Rheumatologie, 52*(6):365–382 (1993).

Elliott, M.J., et al., "Treatment of Rheumatoid Arthritis with Chimeric Monoclonal Antibodies to TNFα", *Rev. Esp. Reumatol, 20* (Suppl. 1):148 (1993); Abstract 320.

Natanson, C., et al., "Selected Treatment Strategies for Septic Shock Based on Proposed Mechanisms of Pathogenesis", *Annals Internal Med., 120*(9):771–783 (1994).

Hervé, P., et al., "Phase I–II Trial of a Monoclonal Anti–Tumor Necrosis Factor α Antibody for the Treatment of Refractory Severe Acute Graft–Versus–Host Disease", *Blood, 79*(12): 3362–3368 (1992).

Thorbecke, G.J., et al., "Involvement of endogenous tumor necrosis factor α and transforming growth factor β during induction of collagen type II arthritis in mice", *Proc. Natl. Acad. Sci. USA, 89*:7375–7379 (1992).

Piguet, P.F., et al., "Evolution of collagen arthritis in mice is arrested by treatment with anti–tumour necrosis factor (TNF) antibody or a recombinant soluble TNF receptor", *Immunology, 77*:510–514 (1992).

Brahn, E., et al., "Effects of Tumor Necrosis Factor and Combination Cyclosporin A/Methotrexate Therapy on Collagen Arthritis", *Arthritis Rheum.,32(4 Suppl.)* S133 (1989); Abstract D42.

Markowitz, J., et al., "Immunology of Inflammatory Bowel Disease: Summary of the Proceedings of the Subcommittee on Immunosupressive Use in IBD", *J. Ped. Gastroenterology Nutrition, 12*:411–423 (1991).

Cohen, S., et al., "Comparison of the Safety and Efficacy of Cyclosporine–A and Methotrexate in Refractory Rheumatoid Arthritis: A Randomized, Multi–Centerd, Placebo–Controlled Trial," *Rev Esp Reumatol* 20 (Suppl. 1):148 (1993); Abstract 318.

Pascalis, L., et al., "Longterm Efficacy and Toxicity of Combined Cyclosporine A–Steroid–Methotrexate Treatment in Rheumatoid Arthritis", *Rev Esp Reumatol 20* (Suppl. 1):148 (1993); Abstract 319.

* cited by examiner

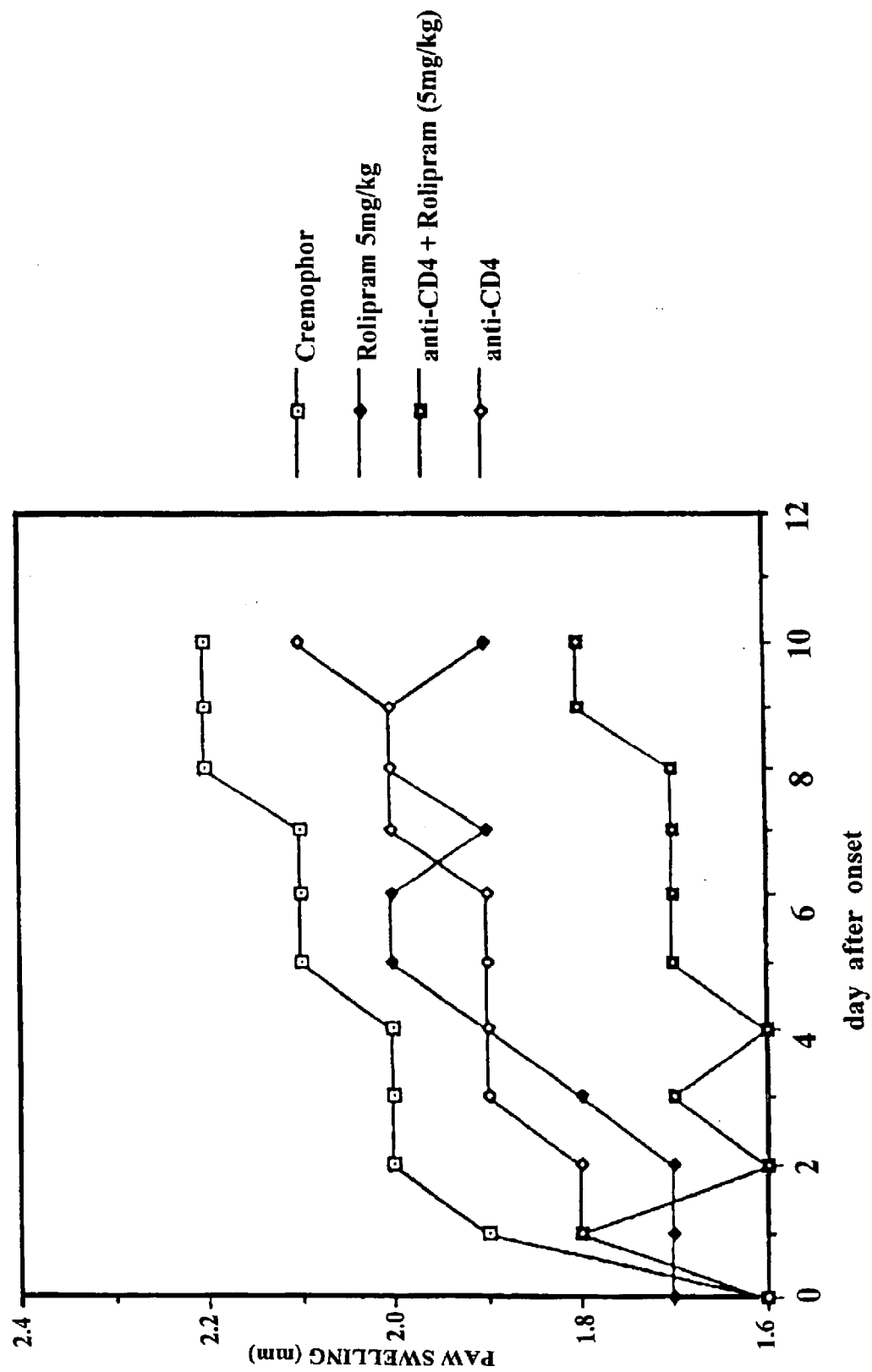

SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
      (A) LENGTH: 22 amino acids
      (B) TYPE: amino acid
      (C) STRANDEDNESS:
      (D) TOPOLOGY: linear (ii) MOLECULE TYPE: peptide (xi) SEQUENCE DESCRIPTION: SEQ ID NO:1:

```
Tyr Ser Gln Val Leu Phe Lys Gly Gln Gly Cys Pro Ser Thr His Val
1               5                   10                  15

Leu Leu Thr His Thr Ile
            20
```

(2) INFORMATION FOR SEQ ID NO:2:

(i) SEQUENCE CHARACTERISTICS:
      (A) LENGTH: 22 amino acids
      (B) TYPE: amino acid
      (C) STRANDEDNESS:
      (D) TOPOLOGY: linear (ii) MOLECULE TYPE: peptide (xi) SEQUENCE DESCRIPTION: SEQ ID NO:2:

```
Tyr Gln Thr Lys Val Asn Leu Leu Ser Ala Ile Lys Ser Pro Cys Gln
1               5                   10                  15

Arg Glu Thr Pro Glu Gly
            20
```

TNFα ANTAGONISTS AND CYCLOSPORIN IN THERAPY OF RHEUMATOID ARTHRITIS

RELATED APPLICATIONS

This application is a continuation of U.S. application Ser. No. 08/607,419, filed Feb. 28, 1996, now abandoned, which is a continuation-in-part of International Application No. PCT/GB94/00462, filed Mar. 10, 1994, which is a continuation-in-part of U.S. application Ser. No. 08/403,785, now U.S. Pat. No. 5,741,488, filed May 3, 1995, which is a continuation-in-part of U.S. application Ser. No. 07/958,248, filed Oct. 8, 1992, now abandoned, the entire teachings of which are incorporated herein by reference.

BACKGROUND OF THE INVENTION

Monocytes and macrophages secrete cytokines known as tumor necrosis factor alpha (TNFα) and tumor necrosis factor beta (TNFβ) in response to endotoxin or other stimuli. TNFα is a soluble homotrimer of 17 kD protein subunits (Smith et al., *J. Biol. Chem.* 262:6951–6954 (1987)). A membrane-bound 26 kD precursor form of TNF also exists (Kriegler et al., *Cell* 53:45–53 (1988)). For reviews of TNF, see Beutler et al., *Nature* 320:584 (1986); Old, *Science* 230:630 (1986); and Le et al., *Lab. Invest.* 56:234 (1987).

Cells other than monocytes or macrophages also produce TNFα. For example, human non-monocytic tumor cell lines produce TNF (Rubin et al., *J. Exp. Med.* 164:1350 (1986); Spriggs et al., *Proc. Natl. Acad. Sci. USA* 84:6563 (1987)). CD4+ and CD8+ peripheral blood T lymphocytes and some cultured T and B cell lines (Cuturi et al., *J. Exp. Med.* 165:1581 (1987); Sung et al., *J. Exp. Med.* 168:1539 (1988); Turner et al., *Eur. J. Immunol.* 17:1807–1814 (1987)) also produce TNFα.

TNF causes pro-inflammatory actions which result in tissue injury, such as inducing procoagulant activity on vascular endothelial cells (Pober et al., *J. Immunol.* 136:1680 (1986)), increasing the adherence of neutrophils and lymphocytes (Pober et al., *J. Immunol.* 138:3319 (1987)), and stimulating the release of platelet activating factor from macrophages, neutrophils and vascular endothelial cells (Camussi et al., *J. Exp. Med.* 166:1390 (1987)).

Recent evidence associates TNF with infections (Cerami et al., *Immunol. Today* 9:28 (1988)), immune disorders, neoplastic pathologies (Oliff et al., *Cell* 50:555 (1987)), autoimmune pathologies and graft-versus-host pathologies (Piguet et al., *J. Exp. Med.* 166:1280 (1987)). The association of TNF with cancer and infectious pathologies is often related to the host's catabolic state. Cancer patients suffer from weight loss, usually associated with anorexia.

The extensive wasting which is associated with cancer, and other diseases, is known as "cachexia" (Kern et al., *J. Parent. Enter. Nutr.* 12:286–298 (1988)). Cachexia includes progressive weight loss, anorexia, and persistent erosion of lean body mass in response to a malignant growth. The fundamental physiological derangement can relate to a decline in food intake relative to energy expenditure. The cachectic state causes most cancer morbidity and mortality. TNF can mediate cachexia in cancer, infectious pathology, and other catabolic states.

TNF also plays a central role in gram-negative sepsis and endotoxic shock (Michie et al., *Br. J. Surg.* 76:670–671 (1989); Debets et al., *Second Vienna Shock Forum*, pp.463–466 (1989); Simpson et al., *Crit. Care Clin.* 5:27–47 (1989)), including fever, malaise, anorexia, and cachexia. Endotoxin strongly activates monocyte/macrophage production and secretion of TNF and other cytokines (Kornbluth et al., *J. Immunol.* 137:2585–2591 (1986)). TNF and other monocyte-derived cytokines mediate the metabolic and neurohormonal responses to endotoxin (Michie et al., *N. Engl. J. Med.* 318:1481–1486 (1988)). Endotoxin administration to human volunteers produces acute illness with flu-like symptoms including fever, tachycardia, increased metabolic rate and stress hormone release (Revhaug et al., *Arch. Surg.* 123:162–170 (1988)). Circulating TNF increases in patients suffering from Gram-negative sepsis (Waage et al., *Lancet* 1:355–357 (1987); Hammerle et al., *Second Vienna Shock Forum* pp. 715–718 (1989); Debets et al., *Crit. Care Med.* 17:489–497 (1989); Calandra et al., *J. Infect. Dis.* 161:982–987 (1990)).

Thus, TNFα has been implicated in inflammatory diseases, autoimmune diseases, viral, bacterial and parasitic infections, malignancies, and/or neurogenerative diseases and is a useful target for specific biological therapy in diseases, such as rheumatoid arthritis and Crohn's disease. Beneficial effects in an open-label trial with a chimeric antibody to TNFα (cA2) have been reported with suppression of inflammation (Elliott et al., *Arthritis Rheum.* 36:1681–1690 (1993)).

SUMMARY OF THE INVENTION

The present invention pertains to the discovery that co-administration of a CD4+ T cell inhibiting agent and a tumor necrosis factor (TNF) antagonist to an individual suffering from a TNF-mediated disease produces a significantly improved response compared to that obtained with administration of the inhibiting agent alone or that obtained with administration of the antagonist alone. As a result of Applicants' invention, a method is provided herein for treating and/or preventing a TNF-mediated disease in an individual comprising co-administering a CD4+ T cell inhibiting agent and a TNF antagonist to the individual in therapeutically effective amounts. The present invention further relates to a method for treating and/or preventing recurrence of a TNF-mediated disease in an individual comprising co-administering a CD4+ T cell inhibiting agent and a TNF antagonist to the individual in therapeutically effective amounts. TNF-mediated diseases include rheumatoid arthritis, Crohn's disease, and acute and chronic immune diseases associated with an allogenic transplantation (e.g., renal, cardiac, bone marrow, liver, pancreatic, small intestine, skin or lung transplantation).

Therefore, in one embodiment, the invention relates to a method of treating and/or preventing rheumatoid arthritis in an individual comprising co-administering a CD4+ T cell inhibiting agent and a TNF antagonist to the individual in therapeutically effective amounts. In a second embodiment, the invention relates to a method of treating and/or preventing Crohn's disease in an individual comprising co-administering a CD4+ T cell inhibiting agent and a TNF antagonist to the individual in therapeutically effective amounts. In a third embodiment, the invention relates to a method of treating and/or preventing acute or chronic immune disease associated with a transplantation in an individual comprising co-administering a CD4+ T cell inhibiting agent and a TNF antagonist to the individual in therapeutically effective amounts.

A further embodiment of the invention relates to compositions comprising a CD4+ T cell inhibiting agent and a TNF antagonist.

CD4+ T cell inhibiting agents useful in the methods and compositions of the present invention include antibodies to T cells or to their receptors, antibodies to antigen presenting cells (APC) or to their receptors, peptides and small molecules blocking the T cell/APC interaction, including those which block the HLA class II groove, or block signal transduction in T-cell activation, such as cyclosporin and cyclosporin analogs, and antibodies to B cells.

TNF antagonists useful in the methods and compositions of the present invention include anti-TNF antibodies and receptor molecules which bind specifically to TNF; compounds which prevent and/or inhibit TNF synthesis, TNF release or its action on target cells, such as thalidomide, tenidap, phosphodiesterase inhibitors (e.g, pentoxifylline and rolipram), A2b adenosine receptor agonists and A2b adenosine receptor enhancers; and compounds which prevent and/or inhibit TNF receptor signalling.

In a particular embodiment of the invention, an inflammatory mediator other than a TNF antagonist can be used instead of or in addition to the TNF antagonist.

BRIEF DESCRIPTION OF THE DRAWINGS

FIGS. 10A and 10B are graphs showing the effect of administering Cremophor EL® (negative control) alone, 5 mg/kg of rolipram alone, 50 μg anti-CD4 antibody alone, and a combination of 5 mg/kg rolipram and 50 μg anti-CD4 antibody to male DBA/1 mice on the suppression of arthritis as assessed by clinical score (FIG. 10A) and paw-swelling (FIG. 10B). Square with black dot=negative control; diamond=rolipram; square with white dot=rolipram plus anti-CD4 antibody; diamond with white dot=anti-CD4 antibody.

DETAILED DESCRIPTION OF THE INVENTION

Figure 1:
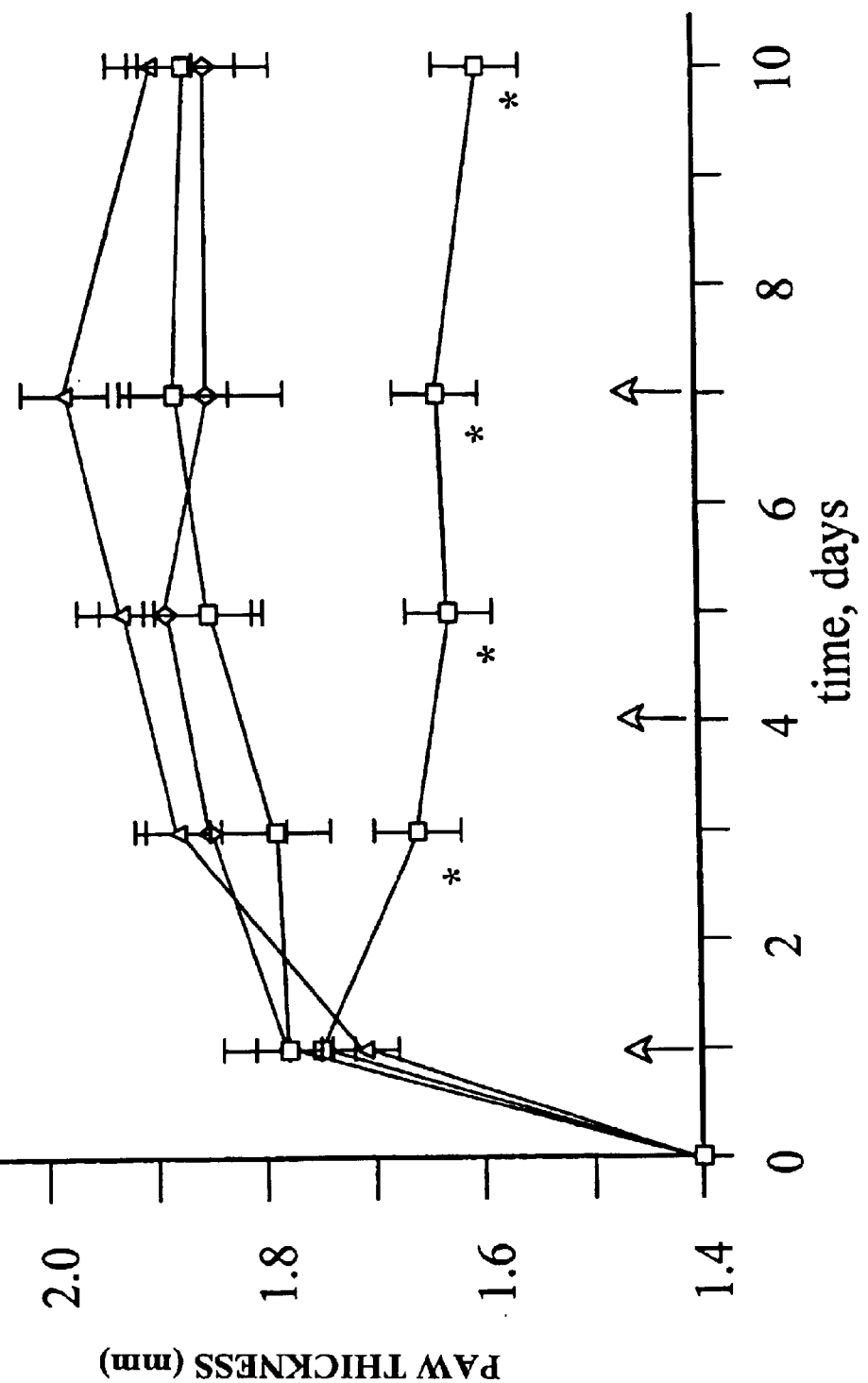
FIG. 1 is a graph showing the effect of administering a sub-optimal dose of anti-TNF antibody (50 μg hamster TN3.19.2) alone and in combination with anti-CD4 antibody (200 μg) to male DBA/1 mice on the suppression of arthritis as assessed by paw-swelling measurements. Triangle= control antibody; diamond=anti-CD4 antibody; open square=anti-TNF antibody; closed square=anti-CD4 antibody plus anti-TNF antibody. An asterisk indicates a significant reduction compared to the group of mice administered control antibody (P<0.05; two-sample t test). Arrows indicate times of injection.

The nature of autoantigens responsible for autoimmune disorders is not known, nor is the action which triggers the autoimmune response. One theory involves the similarity of a viral protein to a self antigen, which results in autoreactive T cells or B cells recognizing a self antigen. Whereas B lymphocytes produce antibodies, thymus-derived or "T cells" are associated with cell-mediated immune functions. T cells recognize antigens presented on the surface of cells and carry out their functions with these antigen-presenting cells.

Various markers have been used to define human T cell populations. CD4 is a non-polymorphic surface glycoprotein receptor with partial sequence identity to immunoglobulins. CD4 receptors define distinct subsets of mature peripheral T cells. In general, CD4 T cells expressing helper or regulatory functions interact with B cells in immune responses, while T cells expressing the CD8 surface antigen function as cytotoxic T cells and have regulatory effects on immune responses. Since T cell receptors are the pathway through which stimuli augment or modulate T cell responses, they present a potential target for immunological intervention.

Of the cellular interactions, that of CD4+ T cells with antigen presenting cells (APC) lies at the root of the immune response. Many aspects of the autoimmune response are essentially similar to that of normal immune responses. Thus, CD4+ autoantigen reactive T cells are restimulated by APC expressing class II with autoantigen peptides in the binding groove. In certain human diseases the evidence that this occurs has been provided: in Graves' disease of the thyroid, in vivo activated T cells are present in the glands that are removed for refractory disease, and many of these cells after cloning can be shown to recognize autologous thyrocytes (as APC) not extrinsically supplied with any antigen, or APC supplied with the thyroid specific antigens thyroid peroxidase or thyroglobulin (Londei, M. et al., Science 228:85–89 (1985); Dayan, C. M. et al., Proc. Natl. Acad. Sci. USA 88:7415–7419 (1991)). Similarly, in rheumatoid arthritis (RA), in vivo activated T cells recognizing collagen type II have been isolated from joints of an RA patient in three consecutive operations during the course of three years (Londei, M. et al., Proc. Natl. Acad. Sci. USA 86:636–640 (1989)). In other human diseases displaying autoimmune characteristics, CD4+ T cells from the blood have been cloned, including CD4+ T cells recognizing the acetylcholine receptor in myasthenia gravis (Hohlfeld, R. et al., Nature 310:224–246 (1984)); myelin basic protein in multiple sclerosis (Hafler, D. A. et al., J. Immunol. 139:68–72 (1987)); or islet cell membranes in insulin dependent diabetes mellitus (De Berardinis, P. et al., Lancet II:823–824 (1988); Kontiainen, S. et al., Autoimmunity 8:193–197 (1991)).

The present invention is directed to a method for treating and/or preventing a TNF-mediated disease in an individual, comprising co-administering a tumor necrosis factor antagonist and a CD4+ T cell inhibiting agent to the individual in therapeutically effective amounts. The TNF antagonist and CD4+ T cell inhibiting agent can be administered simultaneously or sequentially. Multiple CD4+ T cell inhibiting agents and multiple TNF antagonists can be co-administered. Other therapeutic regimens can be used in combination with the therapeutic co-administration of TNF antagonists and CD4+ T cell inhibiting agents.

Inflammatory mediators other than TNF antagonists can be used instead of or in addition to TNF antagonists. As used herein, the term "inflammatory mediator" refers to an agent which decreases, blocks, inhibits, abrogates or interferes with pro-inflammatory mediator activity. Blocking TNF activity in rheumatoid joint cell cultures results in down-regulation of interleukin-1 (IL-1) production (Brennan et al., Lancet 11:244–247 (1989)) and down-regulation of the pro-inflammatory cytokine granulocyte-macrophage colony-stimulating factor (GM-CSF) (Haworth et al., Eur. J. Immunol. 21:2575–2579 (1991); Butler et al., Eur. Cytokine Network 6:225–230 (1995)). Blocking TNF activity also blocks IL-6 and IL-8 production. These cytokine "networks" or "hierarchies" also operate in vivo; rheumatoid arthritis patients treated with anti-TNF antibody reduced their serum IL-6 levels, as well as levels of IL-6 dependent acute phase proteins such as C reactive protein, in the weeks following treatment (Elliott, M. J. et al., Arthritis & Rheumatism 36:1681–1690 (1993)). Since the pro-inflammatory mediators TNF, IL-1, GM-CSF, IL-6 and IL-8 are part of the same network or hierarchy, blocking any of these can have comparable effects. Thus, agents which block TNF, IL-1, GM-CSF, IL-6 and/or IL-8 are useful as the inflammatory mediators of the present invention.

Representative inflammatory mediators that can be used in the present invention include agents which decrease, block, inhibit, abrogate or interfere with IL-1 activity, synthesis, or receptor signalling, such as anti-IL-1 antibody, soluble IL-1R, IL-1 receptor antagonist, or other appropriate peptides and small molecules; agents which decrease, block, inhibit, abrogate or interfere with IL-6 activity, synthesis, or receptor signalling, such as anti-IL-6 antibody, anti-gp130, or other appropriate peptides and small molecules; modalities which decrease, block, inhibit, abrogate or interfere with the activity, synthesis, or receptor signalling of other pro-inflammatory mediators, such as GM-CSF and members of the chemokine (IL-8) family; and cytokines with anti-inflammatory properties, such as IL-4, IL-10, IL-13, and TGFβ. In addition, other anti-inflammatory agents, such as the anti-rheumatic agent methotrexate, can be administered in conjunction with the CD4+ T cell inhibiting agent and/or the TNF antagonist.

The present invention is further directed to a method for treating and/or preventing recurrence of a TNF-mediated disease in an individual comprising co-administering a CD4+ T cell inhibiting agent and a TNF antagonist to the individual in therapeutically effective amounts.

As used herein, a "TNF-mediated disease" refers to a TNF related pathology or disease. TNF related pathologies or diseases include, but are not limited to, the following:

(A) acute and chronic immune and autoimmune pathologies, such as, but not limited to, rheumatoid arthritis (RA), juvenile chronic arthritis (JCA), thyroiditis, graft versus host disease (GVHD), scleroderma, diabetes mellitus, Graves' disease, allergy, acute or chronic immune disease associated with an allogenic transplantation, such as, but not limited to, renal transplantation, cardiac transplantation, bone marrow transplantation, liver transplantation, pancreatic transplantation, small intestine transplantation, lung transplantation and skin transplantation;

(B) infections, including, but not limited to, sepsis syndrome, cachexia, circulatory collapse and shock resulting from acute or chronic bacterial infection, acute and chronic parasitic and/or infectious diseases, bacterial, viral or fungal, such as a human immunodeficiency virus (HIV), acquired immunodeficiency syndrome (AIDS) including symptoms of cachexia, autoimmune disorders, AIDS dementia complex and infections);

(C) inflammatory diseases, such as chronic inflammatory pathologies, including chronic inflammatory pathologies such as, but not limited to, sarcoidosis, chronic inflammatory bowel disease, ulcerative colitis, and Crohn's pathology; vascular inflammatory pathologies, such as, but not limited to, disseminated intravascular coagulation, atherosclerosis, Kawasaki's pathology and vasculitis syndromes, such as, but not limited to, polyarteritis nodosa, Wegener's granulomatosis, Henoch-Schönlein purpura, giant cell arthritis and microscopic vasculitis of the kidneys; chronic active hepatitis; Sjögren's syndrome; spondyloarthropathies, such as ankylosing spondylitis, psoriatic arthritis and spondylitis, enteropathic arthritis and spondylitis, reactive arthritis and arthritis associated with inflammatory bowel disease; and uveitis;

(D) neurodegenerative diseases, including, but not limited to, demyelinating diseases, such as multiple sclerosis and acute transverse myelitis; myasthenia gravis; extrapyramidal and cerebellar disorders, such as lesions of the corticospinal system; disorders of the basal ganglia or cerebellar disorders; hyperkinetic movement disorders, such as Huntington's chorea and senile chorea; drug-induced movement disorders, such as those induced by drugs which block central nervous system (CNS) dopamine receptors; hypokinetic movement disorders, such as Parkinson's disease; progressive supranuclear palsy; cerebellar and spinocerebellar disorders, such as astructural lesions of the cerebellum; spinocerebellar degenerations (spinal ataxia, Friedreich's ataxia, cerebellar cortical degenerations, multiple systems degenerations (Mencel, Dejerine-Thomas, Shi-Drager, and MachadoJoseph)); and systemic disorders (Refsum's disease, abetalipoproteinemia, ataxia, telangiectasia, and mitochondrial multisystem disorder); disorders of the motor unit, such as neurogenic muscular atrophies (anterior horn cell degeneration, such as amyotrophic lateral sclerosis, infantile spinal muscular atrophy and juvenile spinal muscular atrophy); Alzheimer's disease; Down's syndrome in middle age; diffuse Lewy body disease; senile dementia of Lewy body type; Wernicke-Korsakoff syndrome; chronic alcoholism; primary biliary cirrhosis; cryptogenic fibrosing alveolitis and other fibrotic lung diseases; hemolytic anemia; Creutzfeldt-Jakob disease; subacute sclerosing panencephalitis, Hallervorden-Spatz disease; and dementia pugilistica, or any subset thereof;

(E) malignant pathologies involving TNF-secreting tumors or other malignancies involving TNF, such as, but not limited to, leukemias (acute, chronic myelocytic, chronic lymphocytic and/or myelodysplastic syndrome); lymphomas (Hodgkin's and non-Hodgkin's lymphomas, such as malignant lymphomas (Burkitt's lymphoma or Mycosis fungoides));

(F) cachectic syndromes and other pathologies and diseases involving excess TNF, such as, but not limited to, cachexia of cancer, parasitic disease and heart failure; and (G) alcohol-induced hepatitis and other forms of chronic hepatitis.

See, e.g., Berkow et al., Eds., *The Merck Manual,* 16th edition, chapter 11, pp. 1380–1529, Merck and Co., Rahway, N.J., 1992, incorporated herein by reference.

The terms "recurrence", "flare-up" or "relapse" are defined to encompass the reappearance of one or more symptoms of the disease state. For example, in the case of rheumatoid arthritis, a recurrence can include the experience of one or more of swollen joints, morning stiffness or joint tenderness.

In one embodiment, the invention relates to a method of treating and/or preventing rheumatoid arthritis in an individual comprising co-administering a CD4+ T cell inhibiting agent and a TNF antagonist to the individual in therapeutically effective amounts.

In a second embodiment, the invention relates to a method for treating and/or preventing Crohn's disease in an individual comprising co-administering a CD4+ T cell inhibiting agent and a TNF antagonist to the individual in therapeutically effective amounts.

In a third embodiment, the invention relates to a method for treating and/or preventing an acute or chronic immune disease associated with an allogenic transplantation in an individual comprising co-administering a CD4+ T cell inhibiting agent and a TNF antagonist to the individual in therapeutically effective amounts. As used herein, a "transplantation" includes renal transplantation, cardiac transplantation, bone marrow transplantation, liver transplantation, pancreatic transplantation, small intestine transplantation, skin transplantation and lung transplantation.

The benefits of combination therapy with TNF antagonists and CD4+ T cell inhibiting agents include significantly improved response in comparison with the effects of treatment with each therapeutic modality separately. In addition, lower dosages can be used to provide the same reduction of the immune and inflammatory response, thus increasing the therapeutic window between a therapeutic and a toxic effect. Lower doses also results in lower financial costs to the patient, and potentially fewer side effects. For example, immune and/or allergic responses to TNF antagonists can be reduced, thus enhancing safety and therapeutic efficacy.

In a further embodiment, the invention relates to compositions comprising a TNF antagonist and a CD4+ T cell inhibiting agent. The compositions of the present invention are useful for treating a subject having a pathology or condition associated with abnormal levels of a substance reactive with a TNF antagonist, in particular TNF in excess of, or less than, levels present in a normal healthy subject, where such excess or diminished levels occur in a systemic, localized or particular tissue type or location in the body. Such tissue types can include, but are not limited to, blood, lymph, central nervous system (CNS), liver, kidney, spleen, heart muscle or blood vessels, brain or spinal cord white matter or grey matter, cartilage, ligaments, tendons, lung, pancreas, ovary, testes, prostate. Increased or decreased TNF concentrations relative to normal levels can also be localized to specific regions or cells in the body, such as joints, nerve blood vessel junctions, bones, specific tendons or ligaments, or sites of infection, such as bacterial or viral infections.

Tumor Necrosis Factor Antagonists

As used herein, a "tumor necrosis factor antagonist" decreases, blocks, inhibits, abrogates or interferes with TNF activity in vivo. For example, a suitable TNF antagonist can bind TNF and includes anti-TNF antibodies and receptor molecules which bind specifically to TNF. A suitable TNF antagonist can also prevent or inhibit TNF synthesis and/or TNF release and includes compounds such as thalidomide, tenidap, and phosphodiesterase inhibitors, such as, but not limited to, pentoxifylline and rolipram. A suitable TNF antagonist that can prevent or inhibit TNF synthesis and/or TNF release also includes A2b adenosine receptor enhancers and A2b adenosine receptor agonists (e.g., 5'-(N-cyclopropyl)-carboxamidoadenosine, 5'-N-ethylcarboxamidoadenosine, cyclohexyladenosine and R-$N^6$-phenyl-2-propyladenosine). See, for example, Jacobson (GB 2 289 218 A), the teachings of which are entirely incorporated herein by reference. A suitable TNF antagonist can also prevent or inhibit TNF receptor signalling.

Anti-TNF Antibodies

Anti-TNF antibodies useful in the methods and compositions of the present invention include monoclonal, chimeric, humanized, resurfaced and recombinant antibodies and fragments thereof which are characterized by high affinity binding to TNF and low toxicity (including human anti-murine antibody (HAMA) and/or human anti-chimeric antibody (HACA) response). In particular, an antibody where the individual components, such as the variable region, constant region and framework, individually and/or collectively possess low immunogenicity is useful in the present invention. The antibodies which can be used in the invention are characterized by their ability to treat patients for extended periods with good to excellent alleviation of symptoms and low toxicity. Low immunogenicity and/or high affinity, as well as other undefined properties, may contribute to the therapeutic results achieved.

An example of a high affinity monoclonal antibody useful in the methods and compositions of the present invention is murine monoclonal antibody (mAb) A2 and antibodies which will competitively inhibit in vivo the binding to human TNFα of anti-TNFα murine mAb A2 or an antibody having substantially the same specific binding characteristics, as well as fragments and regions thereof. Murine monoclonal antibody A2 and chimeric derivatives thereof, such as cA2, are described in U.S. application Ser. No. 08/192,102 (filed Feb. 4, 1994; now U.S. Pat. No. 5,656,272), U.S. application Ser. No. 08/192,861 (filed Feb. 4, 1994; now U.S. Pat. No. 5,919,452), U.S. application Ser. No. 08/192,093 (filed Feb. 4, 1994), U.S. application Ser. No. 08/324,799 (filed Oct. 18, 1994; now U.S. Pat. No. 5,698,195) and Le, J. et al., International Publication No. WO 92/16553 (published Oct. 1, 1992), which references are entirely incorporated herein by reference. A second example of a high affinity monoclonal antibody useful in the methods and compositions of the present invention is murine mAb 195 and antibodies which will competitively inhibit in vivo the binding to human TNFα of anti-TNFα murine 195 or an antibody having substantially the same specific binding characteristics, as well as fragments and regions thereof. Other high affinity monoclonal antibodies useful in the methods and compositions of the present invention include murine mAb 114 and murine mAb 199 and antibodies which will competitively inhibit in vivo the binding to human TNFα of anti-TNFα murine mAb 114 or mAb 199 or an antibody having substantially the same specific binding characteristics of mAb 114 or mAb 199, as well as fragments and regions thereof. Murine monoclonal antibodies 114, 195 and 199 and the method for producing them are described by Möller, A. et al. (*Cytokine* 2(3):162–169 (1990)), the teachings of which are entirely incorporated herein by reference. Preferred methods for determining mAb specificity and affinity by competitive inhibition can be found in Harlow et al., *Antibodies: A Laboratory Manual*, Cold Spring Harbor Laboratory Press, Cold Spring Harbor, New York (1988); Colligan et al., Eds., *Current Protocols in Immunology*, Greene Publishing Assoc. and Wiley Interscience, New York (1992, 1993); Kozbor et al., *Immunol. Today* 4:72–79 (1983); Ausubel et al., eds. *Current Protocols in Molecular Biology*, Wiley Interscience, New York (1987, 1992, 1993); and Muller, *Meth. Enzymol.* 92:589–601 (1983), which references are entirely incorporated herein by reference.

Additional examples of monoclonal anti-TNF antibodies that can be used in the present invention are described in the art (see, e.g., U.S. application Ser. No. 07/943,852 (filed Sep. 11, 1992); Rathjen et al., International Publication No. WO 91/02078 (published Feb. 21, 1991); Rubin et al., EPO Patent Publication 0218868 (published Apr. 22, 1987); Yone et al., EPO Patent Publication 0288088 (Oct. 26, 1988); Liang et al., *Biochem. Biophys. Res. Comm.* 137:847–854 (1986); Meager, et al., *Hybridoma* 6:305–311 (1987); Fendly et al., *Hybridoma* 6:359–369 (1987); Bringman et al., *Hybridoma* 6:489–507 (1987); Hirai et al., *J. Immunol. Meth.* 96:57–62 (1987); Moller et al., *Cytokine* 2:162–169 (1990), which references are entirely incorporated herein by reference).

Chimeric antibodies are immunoglobulin molecules characterized by two or more segments or portions derived from different animal species. Generally, the variable region of the chimeric antibody is derived from a non-human mammalian antibody, such as a murine mAb, and the immunoglobulin constant region is derived from a human immunoglobulin molecule. Preferably, a variable region with low immunogenicity is selected and combined with a human constant region which also has low immunogenicity, the combination also preferably having low immunogenicity. "Low" immunogenicity is defined herein as raising significant HACA or HAMA responses in less than about 75%, or preferably less than about 50% of the patients treated and/or raising low titres in the patient treated (less than about 300, preferably less than about 100 measured with a double antigen enzyme immunoassay) (Elliott et al., *Lancet* 344:1125–1127 (1994), incorporated herein by reference).

As used herein, the term "chimeric antibody" includes monovalent, divalent or polyvalent immunoglobulins. A monovalent chimeric antibody is a dimer (HL) formed by a chimeric H chain associated through disulfide bridges with a chimeric L chain. A divalent chimeric antibody is a tetramer (H2L2) formed by two HL dimers associated through at least one disulfide bridge. A polyvalent chimeric antibody can also be produced, for example, by employing a CH region that aggregates (e.g., from an IgM H chain, or μ chain).

Antibodies comprise individual heavy (H) and/or light (L) immunoglobulin chains. A chimeric H chain comprises an antigen binding region derived from the H chain of a non-human antibody specific for TNF, which is linked to at least a portion of a human H chain C region (CH), such as CH1 or CH2. A chimeric L chain comprises an antigen binding region derived from the L chain of a non-human antibody specific for TNF, linked to at least a portion of a human L chain C region (CL).

Chimeric antibodies and methods for their production have been described in the art (Morrison et al., *Proc. Natl. Acad. Sci. USA* 81:6851–6855 (1984); Boulianne et al., *Nature* 312:643–646 (1984); Neuberger et al., *Nature* 314:268–270 (1985); Taniguchi et al., European Patent Application 171496 (published Feb. 19, 1985); Morrison et al., European Patent Application 173494 (published Mar. 5, 1986); Neuberger et al., PCT Application WO 86/01533, (published Mar. 13, 1986); Kudo et al., European Patent Application 184187 (published Jun. 11, 1986); Morrison et al., European Patent Application 173494 (published Mar. 5, 1986); Sahagan et al., *J. Immunol.* 137:1066–1074 (1986); Robinson et al., International Publication No. PCT/US86/02269 (published May 7, 1987); Liu et al., *Proc. Natl. Acad. Sci. USA* 84:3439–3443 (1987); Sun et al., *Proc. Natl. Acad. Sci. USA* 84:214–218 (1987); Better et al., *Science* 240:1041–1043 (1988); and Harlow and Lane, *Antibodies: A Laboratory Manual*, Cold Spring Harbor Laboratory, New York, 1988). These references are entirely incorporated herein by reference.

The anti-TNF chimeric antibody can comprise, for example, two light chains and two heavy chains, each of the chains comprising at least part of a human constant region and at least part of a variable (V) region of non-human origin having specificity to human TNF, said antibody binding with high affinity to an inhibiting and/or neutralizing epitope of human TNF, such as the antibody cA2. The antibody also includes a fragment or a derivative of such an antibody, such as one or more portions of the antibody chain, such as the heavy chain constant or variable regions, or the light chain constant or variable regions.

Humanizing and resurfacing the antibody can further reduce the immunogenicity of the antibody. See, for example, Winter (U.S. Pat. No. 5,225,539 and EP 239,400 B1), Padlan et al. (EP 519,596 A1) and Pedersen et al. (EP 592,106 A1) incorporated herein by reference.

Preferred antibodies useful in the methods and compositions of the present invention are high affinity human-murine chimeric anti-TNF antibodies, and fragments or regions thereof, that have potent inhibiting and/or neutralizing activity in vivo against human TNFα. Such antibodies and chimeric antibodies can include those generated by immunization using purified recombinant TNFα or peptide fragments thereof comprising one or more epitopes.

An example of such a chimeric antibody is cA2 and antibodies which will competitively inhibit in vivo the binding to human TNFα of anti-TNFα murine mAb A2, chimeric mAb cA2, or an antibody having substantially the same specific binding characteristics, as well as fragments and regions thereof. Chimeric mAb cA2 has been described, for example, in U.S. application Ser. No. 08/192,102 (filed Feb. 4, 1994; now U.S. Pat. No. 5,656,272), U.S. application Ser. No. 08/192,861 (filed Feb. 4, 1994), U.S. application Ser. No. 08/192,093 (filed Feb. 4, 1994) and U.S. application Ser. No. 08/324,799 (filed on Oct. 18, 1994; now U.S. Pat. No. 5,698,195) and by Le, J. et al., International Publication No. WO 92/16553 (published Oct. 1, 1992); Knight, D. M. et al. (*Mol. Immunol.* 30:1443–1453 (1993)); and Siegel, S. A. et al. (*Cytokine* 7(1):15–25 (1995)), which references are entirely incorporated herein by reference.

Chimeric A2 anti-TNF consists of the antigen binding variable region of the high-affinity neutralizing mouse anti-human TNF IgG1 antibody, designated A2, and the constant regions of a human IgG1, kappa immunoglobulin. The human IgG1 Fc region improves allogeneic antibody effector function, increases the circulating serum half-life and decreases the immunogenicity of the antibody. The avidity and epitope specificity of the chimeric A2 is derived from the variable region of the murine A2. Chimeric A2 neutralizes the cytotoxic effect of both natural and recombinant human TNF in a dose dependent manner. From binding assays of cA2 and recombinant human TNF, the affinity constant of cA2 was calculated to be $1.8 \times 10^9 M^{-1}$. Preferred methods for determining mAb specificity and affinity by competitive inhibition can be found in Harlow, et al., *Antibodies: A Laboratory Manual*, Cold Spring Harbor Laboratory Press, Cold Spring Harbor, N.Y., 1988; Colligan et al., Eds., *Current Protocols in Immunology*, Greene Publishing Assoc. and Wiley Interscience, New York, (1992, 1993); Kozbor et al., *Immunol. Today* 4:72–79 (1983); Ausubel et al., Eds. *Current Protocols in Molecular Biology*, Wiley Interscience, New York (1987, 1992, 1993); and Muller, *Meth. Enzymol.* 92:589–601 (1983), which references are entirely incorporated herein by reference.

As used herein, the term "antigen binding region" refers to that portion of an antibody molecule which contains the amino acid residues that interact with an antigen and confer on the antibody its specificity and affinity for the antigen. The antibody region includes the "framework" amino acid residues necessary to maintain the proper conformation of the antigen-binding residues. Generally, the antigen binding region will be of murine origin. In other embodiments, the antigen binding region can be derived from other animal species, such as sheep, rabbit, rat or hamster. Preferred sources for the DNA encoding such a non-human antibody include cell lines which produce antibody, preferably hybrid cell lines commonly known as hybridomas. In one embodiment, a preferred hybridoma is the A2 hybridoma cell line.

An "antigen" is a molecule or a portion of a molecule capable of being bound by an antibody which is additionally capable of inducing an animal to produce antibody capable of selectively binding to an epitope of that antigen. An antigen can have one or more than one epitope.

The term "epitope" is meant to refer to that portion of the antigen capable of being recognized by and bound by an antibody at one or more of the antibody's antigen binding region. Epitopes usually consist of chemically active surface groupings of molecules such as amino acids or sugar side chains and have specific three dimensional structural characteristics as well as specific charge characteristics. By "inhibiting and/or neutralizing epitope" is intended an epitope, which, when bound by an antibody, results in loss of biological activity of the molecule containing the epitope, in vivo or in vitro, more preferably in vivo, including binding of TNF to a TNF receptor. Epitopes of TNF have been identified within amino acids 1 to about 20, about 56 to about 77, about 108 to about 127 and about 138 to about 149. Preferably, the antibody binds to an epitope comprising at least about 5 amino acids of TNF within TNF residues from about 87 to about 107, about 59 to about 80 or a combination thereof. Generally, epitopes include at least about 5 amino acids and less than about 22 amino acids embracing or overlapping one or more of these regions.

For example, epitopes of TNF which are recognized by, and/or binds with anti-TNF activity, an antibody, fragments, and variable regions thereof, include:

59–80: Tyr-Ser-Gln-Val-Leu-Phe-Lys-Gly-Gln-Gly-Cys-Pro-Ser-Thr-His-Val-Leu-Leu-Thr-His-Thr-Ile     (SEQ ID NO: 1);

and/or

87–108: Tyr-Gln-Thr-Lys-Val-Asn-Leu-Leu-Ser-Ala-Ile-Lys-Ser-Pro-Cys-Gln-Arg-Glu-Thr-Pro-Glu-Gly     (SEQ ID NO:2).

The anti-TNF antibodies, fragments, and variable regions thereof, that are recognized by, and/or bind with anti-TNF activity, these epitopes block the action of TNFα without binding to the putative receptor binding locus as presented by Eck and Sprang (*J. Biol. Chem.* 264(29): 17595–17605 (1989) (amino acids 11–13, 37–42, 49–57 and 155–157 of hTNFα). Rathjen et al., International Publication WO 91/02078 (published Feb. 21, 1991), incorporated herein by reference, discloses TNF ligands which can bind additional epitopes of TNF.

Antibody Production Using Hybridomas

The techniques to raise antibodies to small peptide sequences that recognize and bind to those sequences in the free or conjugated form or when presented as a native sequence in the context of a large protein are well known in the art. Such antibodies can be produced by hybridoma or recombinant techniques known in the art.

Murine antibodies which can be used in the preparation of the antibodies useful in the methods and compositions of the present invention have also been described in Rubin et al., EP0218868 (published Apr. 22, 1987); Yone et al., EP0288088 (published Oct. 26, 1988); Liang et al., *Biochem. Biophys. Res. Comm.* 137:847–854 (1986); Meager, et al., *Hybridoma* 6:305–311 (1987); Fendly et al., *Hybridoma* 6:359–369 (1987); Bringman et al., *Hybridoma* 6:489–507 (1987); Hirai et al., *J. Immunol. Meth.* 96:57–62 (1987); Möller et al., *Cytokine* 2:162–169 (1990).

The cell fusions are accomplished by standard procedures well known to those skilled in the field of immunology. Fusion partner cell lines and methods for fusing and selecting hybridomas and screening for mAbs are well known in the art. See, e.g, Ausubel infra, Harlow infra, and Colligan infra, the contents of which references are incorporated entirely herein by reference.

The TNFα-specific murine mAb useful in the methods and compositions of the resent invention can be produced in large quantities by injecting hybridoma or transfectoma cells secreting the antibody into the peritoneal cavity of mice and, after appropriate time, harvesting the ascites fluid which contains a high titer of the mAb, and isolating the mAb therefrom. For such in vivo production of the mAb with a hybridoma (e.g., rat or human), hybridoma cells are preferably grown in irradiated or athymic nude mice. Alternatively, the antibodies can be produced by culturing hybridoma or transfectoma cells in vitro and isolating secreted mAb from the cell culture medium or recombinantly, in eukaryotic or prokaryotic cells.

In one embodiment, the antibody used in the methods and compositions of the present invention is a mAb which binds amino acids of an epitope of TNF recognized by A2, rA2 or cA2, produced by a hybridoma or by a recombinant host. In another embodiment, the antibody is a chimeric antibody which recognizes an epitope recognized by A2. In still another embodiment, the antibody is a chimeric antibody designated as chimeric A2 (cA2).

As examples of antibodies useful in the methods and compositions of the present invention, murine mAb A2 is produced by a cell line designated c134A. Chimeric antibody cA2 is produced by a cell line designated c168A.

"Derivatives" of the antibodies including fragments, regions or proteins encoded by truncated or modified genes to yield molecular species functionally resembling the immunoglobulin fragments are also useful in the methods and compositions of the present invention. The modifications include, but are not limited to, addition of genetic sequences coding for cytotoxic proteins such as plant and bacterial toxins. The fragments and derivatives can be produced from appropriate cells, as is known in the art. Alternatively, anti-TNF antibodies, fragments and regions can be bound to cytotoxic proteins or compounds in vitro, to provide cytotoxic anti-TNF antibodies which would selectively kill cells having TNF on their surface.

"Fragments" of the antibodies include, for example, Fab, Fab', F(ab')$_2$ and Fv. These fragments lack the Fc fragment of intact antibody, clear more rapidly from the circulation, and can have less non-specific tissue binding than an intact antibody (Wahl et al., *J. Nucl. Med.* 24:316–325 (1983)). These fragments are produced from intact antibodies using methods well known in the art, for example by proteolytic cleavage with enzymes such as papain (to produce Fab fragments) or pepsin (to produce F(ab')$_2$ fragments).

Recombinant Expression of Anti-TNF Antibodies

Recombinant and/or chimeric murine-human or human-human antibodies that inhibit TNF can be provided using known techniques based on the teachings provided in U.S. application Ser. No. 08/192,102 (filed Feb. 4, 1994; now U.S. Pat. No. 5,656,272), U.S. application Ser. No. 08/192,861 (filed Feb. 4, 1994; now U.S. Pat. No. 5,919,452), U.S. application Ser. No. 08/192,093 (filed Feb. 4, 1994), U.S. application Ser. No. 08/324,799 (filed on Oct. 18, 1994; now U.S. Pat. No. 5,698,195) and Le, J. et al., International Publication No. WO 92/16553 (published Oct. 1, 1992), which references are entirely incorporated herein by reference. See, e.g., Ausubel et al., Eds. *Current Protocols in Molecular Biology*, Wiley Interscience, New York (1987, 1992, 1993); and Sambrook et al. *Molecular Cloning: A Laboratory Manual*, Cold Spring Harbor Laboratory Press, New York, 1989, the contents of which are entirely incorporated herein by reference. See also, e.g., Knight, D. M., et al., *Mol. Immunol* 30:1443–1453 (1993); and Siegel, S. A. et al., *Cytokine* 7(1):15–25 (1995), the contents of which are entirely incorporated herein by reference.

The DNA encoding an anti-TNF antibody can be genomic DNA or cDNA which encodes at least one of the heavy chain constant region (Hc), the heavy chain variable region (Hc), the light chain variable region (Lv) and the light chain constant regions (Lc). A convenient alternative to the use of chromosomal gene fragments as the source of DNA encoding the murine V region antigen-binding segment is the use of cDNA for the construction of chimeric immunoglobulin genes, e.g., as reported by Liu et al. (*Proc. Natl. Acad. Sci., USA* 84:3439 (1987) and *J. Immunology* 139:3521 (1987)), which references are entirely incorporated herein by reference. The use of cDNA requires that gene expression elements appropriate for the host cell be combined with the gene in order to achieve synthesis of the desired protein. The use of cDNA sequences is advantageous over genomic sequences (which contain introns), in that cDNA sequences can be expressed in bacteria or other hosts which lack appropriate RNA splicing systems. An example of such a preparation is set forth below.

Because the genetic code is degenerate, more than one codon can be used to encode a particular amino acid. Using the genetic code, one or more different oligonucleotides can be identified, each of which would be capable of encoding the amino acid. The probability that a particular oligonucleotide will, in fact, constitute the actual XXX-encoding sequence can be estimated by considering abnormal base pairing relationships and the frequency with which a particular codon is actually used (to encode a particular amino acid) in eukaryotic or prokaryotic cells expressing an anti-TNF antibody or fragment. Such "codon usage rules" are disclosed by Lathe, et al., *J. Mol. Biol.* 183:1–12 (1985). Using the "codon usage rules" of Lathe, a single oligonucleotide, or a set of oligonucleotides, that contains a theoretical "most probable" nucleotide sequence capable of encoding anti-TNF variable or constant region sequences is identified.

Although occasionally an amino acid sequence can be encoded by only a single oligonucleotide, frequently the amino acid sequence can be encoded by any of a set of similar oligonucleotides. Importantly, whereas all of the members of this set contain oligonucleotides which are capable of encoding the peptide fragment and, thus, potentially contain the same oligonucleotide sequence as the gene which encodes the peptide fragment, only one member of the set contains the nucleotide sequence that is identical to the nucleotide sequence of the gene. Because this member is present within the set, and is capable of hybridizing to DNA even in the presence of the other members of the set, it is possible to employ the unfractionated set of oligonucleotides in the same manner in which one would employ a single oligonucleotide to clone the gene that encodes the protein.

The oligonucleotide, or set of oligonucleotides, containing the theoretical "most probable" sequence capable of encoding an anti-TNF antibody or fragment including a variable or constant region is used to identify the sequence of a complementary oligonucleotide or set of oligonucleotides which is capable of hybridizing to the "most probable" sequence, or set of sequences. An oligonucleotide containing such a complementary sequence can be employed as a probe to identify and isolate the variable or constant region anti-TNF gene (Sambrook et al., infra).

A suitable oligonucleotide, or set of oligonucleotides, which is capable of encoding a fragment of the variable or constant anti-TNF region (or which is complementary to such an oligonucleotide, or set of oligonucleotides) is identified (using the above-described procedure), synthesized, and hybridized by means well known in the art, against a DNA or, more preferably, a cDNA preparation derived from cells which are capable of expressing anti-TNF antibodies or variable or constant regions thereof Single stranded oligonucleotide molecules complementary to the "most probable"

variable or constant anti-TNF region peptide coding sequences can be synthesized using procedures which are well known to those of ordinary skill in the art (Belagaje et al., *J. Biol. Chem.* 254:5765–5780 (1979); Maniatis et al., in: *Molecular Mechanisms in the Control of Gene Expression*, Nierlich et al., Eds., Acad. Press, New York (1976); Wu et al., *Prog. Nucl. Acid Res. Mol. Biol.* 21:101–141 (1978); Khorana, *Science* 203:614–625 (1979)). Additionally, DNA synthesis can be achieved through the use of automated synthesizers. Techniques of nucleic acid hybridization are disclosed by Sambrook et al., *Molecular Cloning: A Laboratory Manual*, Cold Spring Harbor Laboratory Press, New York, 1989; and by Haynes et al., in: *Nucleic Acid Hybridization: A Practical Approach*, IRL Press, Washington, D.C. (1985), which references are entirely incorporated herein by reference. Techniques such as, or similar to, those described above have successfully enabled the cloning of genes for human aldehyde dehydrogenases (Hsu et al., *Proc. Natl. Acad. Sci. USA* 82:3771–3775 (1985)), fibronectin (Suzuki et al., *Bur. Mol. Biol. Organ. J.* 4:2519–2524 (1985)), the human estrogen receptor gene (Walter et al., *Proc. Natl. Acad. Sci. USA* 82:7889–7893 (1985)), tissue-type plasminogen activator (Pennica et al., *Nature* 301:214–221 (1983)) and human placental alkaline phosphatase complementary DNA (Keun et al., *Proc. Natl. Acad. Sci. USA* 82:8715–8719 (1985)).

In an alternative way of cloning a polynucleotide encoding an anti-TNF variable or constant region, a library of expression vectors is prepared by cloning DNA or, more preferably, cDNA (from a cell capable of expressing an anti-TNF antibody or variable or constant region) into an expression vector. The library is then screened for members capable of expressing a protein which competitively inhibits the binding of an anti-TNF antibody, such as A2 or cA2, and which has a nucleotide sequence that is capable of encoding polypeptides that have the same amino acid sequence as anti-TNF antibodies or fragments thereof In this embodiment, DNA, or more preferably cDNA, is extracted and purified from a cell which is capable of expressing an anti-TNF antibody or fragment. The purified cDNA is fragmentized (by shearing, endonuclease digestion, etc.) to produce a pool of DNA or cDNA fragments. DNA or cDNA fragments from this pool are then cloned into an expression vector in order to produce a genomic library of expression vectors whose members each contain a unique cloned DNA or cDNA fragment such as in a lambda phage library, expression in prokaryotic cell (e.g., bacteria) or eukaryotic cells, (e.g., mammalian, yeast, insect or, fungus). See, e.g., Ausubel, infra, Harlow, infra, Colligan, infra; Nyyssonen et al. *Bio/Technology* 11:591–595 (1993); Marks et al., *Bio/Technology* 11:1145–1149 (October 1993). Once nucleic acid encoding such variable or constant anti-TNF regions is isolated, the nucleic acid can be appropriately expressed in a host cell, along with other constant or variable heavy or light chain encoding nucleic acid, in order to provide recombinant monoclonal antibodies that bind TNF with inhibitory activity. Such antibodies preferably include a murine or human anti-TNF variable region which contains a framework residue having complementarity determining residues which are responsible for antigen binding.

Human genes which encode the constant (C) regions of the chimeric antibodies, fragments and regions of the present invention can be derived from a human fetal liver library, by known methods. Human C region genes can be derived from any human cell including those which express and produce human immunoglobulins. The human CH region can be derived from any of the known classes or isotypes of human H chains, including gamma, $\mu$, $\alpha$, $\delta$ or $\epsilon$, and subtypes thereof, such as G1, G2, G3 and G4. Since the H chain isotype is responsible for the various effector functions of an antibody, the choice of CH region will be guided by the desired effector functions, such as complement fixation, or activity in antibody-dependent cellular cytotoxicity (ADCC). Preferably, the CH region is derived from gamma 1 (IgG1), gamma 3 (IgG3), gamma 4 (IgG4), or $\mu$ (IgM). The human CL region can be derived from either human L chain isotype, kappa or lambda.

Genes encoding human immunoglobulin C regions are obtained from human cells by standard cloning techniques (see, e.g., Sambrook et al., *Molecular Cloning: A Laboratory Manual,* 2nd Edition, Cold Spring Harbor Press, Cold Spring Harbor, N.Y., 1989; and Ausubel et al., Eds., *Current Protocols in Molecular Biology*, Wiley Interscience, New York (1987–1993)). Human C region genes are readily available from known clones containing genes representing the two classes of L chains, the five classes of H chains and subclasses thereof Chimeric antibody fragments, such as $F(ab')_2$ and Fab, can be prepared by designing a chimeric H chain gene which is appropriately truncated. For example, a chimeric gene encoding an H chain portion of an $F(ab')_2$ fragment would include DNA sequences encoding the CH1 domain and hinge region of the H chain, followed by a translational stop codon to yield the truncated molecule.

Generally, the murine, human and chimeric antibodies, fragments and regions are produced by cloning DNA segments encoding the H and L chain antigen-binding regions of a TNF-specific antibody, and joining these DNA segments to DNA segments encoding CH and CL regions, respectively, to produce murine, human or chimeric immunoglobulin-encoding genes. Thus, in a preferred embodiment, a fused chimeric gene is created which comprises a first DNA segment that encodes at least the antigen-binding region of non-human origin, such as a functionally rearranged V region with joining (J) segment, linked to a second DNA segment encoding at least a part of a human C region.

Therefore, cDNA encoding the antibody V and C regions and the method of producing a chimeric antibody can involve several steps, outlined below:

1. isolation of messenger RNA (mRNA) from the cell line producing an anti-TNF antibody and from optional additional antibodies supplying heavy and light constant regions; cloning and cDNA production therefrom;
2. preparation of a full length cDNA library from purified mRNA from which the appropriate V and/or C region gene segments of the L and H chain genes can be: (i) identified with appropriate probes, (ii) sequenced, and (iii) made compatible with a C or V gene segment from another antibody for a chimeric antibody;
3. Construction of complete H or L chain coding sequences by linkage of the cloned specific V region gene segments to cloned C region gene, as described above;
4. Expression and production of L and H chains in selected hosts, including prokaryotic and eukaryotic cells to provide murine-murine, human-murine or human-human antibodies.

One common feature of all immunoglobulin H and L chain genes and their encoded mRNAs is the J region. H and L chain J regions have different sequences, but a high degree of sequence homology exists (greater than 80%) among each group, especially near the C region. This homology is exploited in this method and consensus sequences of H and L chain J regions can be used to design oligonucleotides for use as primers for introducing useful restriction sites into the J region for subsequent linkage of V region segments to human C region segments.

C region cDNA vectors prepared from human cells can be modified by site-directed mutagenesis to place a restriction site at the analogous position in the human sequence. For example, one can clone the complete human kappa chain C (Ck) region and the complete human gamma-1 C region (C gamma-1). In this case, the alternative method based upon genomic C region clones as the source for C region vectors would not allow these genes to be expressed in bacterial systems where enzymes needed to remove intervening sequences are absent. Cloned V region segments are excised and ligated to L or H chain C region vectors. Alternatively, the human C gamma-1 region can be modified by introducing a termination codon thereby generating a gene sequence which encodes the H chain portion of an Fab molecule. The coding sequences with linked V and C regions are then transferred into appropriate expression vehicles for expression in appropriate hosts, prokaryotic or eukaryotic.

Two coding DNA sequences are said to be "operably linked" if the linkage results in a continuously translatable sequence without alteration or interruption of the triplet reading frame. A DNA coding sequence is operably linked to a gene expression element if the linkage results in the proper function of that gene expression element to result in expression of the coding sequence.

Expression vehicles include plasmids or other vectors. Preferred among these are vehicles carrying a functionally complete human CH or CL chain sequence having appropriate restriction sites engineered so that any VH or VL chain sequence with appropriate cohesive ends can be easily inserted therein. Human CH or CL chain sequence-containing vehicles thus serve as intermediates for the expression of any desired complete H or L chain in any appropriate host.

A chimeric antibody, such as a mouse-human or human-human, will typically be synthesized from genes driven by the chromosomal gene promoters native to the mouse H and L chain V regions used in the constructs, splicing usually occurs between the splice donor site in the mouse J region and the splice acceptor site preceding the human C region and also at the splice regions that occur within the human C, region; polyadenylation and transcription termination occur at native chromosomal sites downstream of the human coding regions.

A nucleic acid sequence encoding at least one anti-TNF antibody fragment may be recombined with vector DNA in accordance with conventional techniques, including blunt-ended or staggered-ended termini for ligation, restriction enzyme digestion to provide appropriate termini, filling in of cohesive ends as appropriate, alkaline phosphatase treatment to avoid undesirable joining, and ligation with appropriate ligases. Techniques for such manipulations are disclosed, e.g., by Ausubel, supra, Sambrook, supra, entirely incorporated herein by reference, and are well known in the art.

A nucleic acid molecule, such as DNA, is "capable of expressing" a polypeptide if it contains nucleotide sequences which contain transcriptional and translational regulatory information and such sequences are "operably linked" to nucleotide sequences which encode the polypeptide. An operable linkage is a linkage in which the regulatory DNA sequences and the DNA sequence sought to be expressed are connected in such a way as to permit gene expression as anti-TNF peptides or antibody fragments in recoverable amounts. The precise nature of the regulatory regions needed for gene expression may vary from organism to organism and is well known in the analogous art. See, e.g., Sambrook et al., *Molecular Cloning: A Laboratory Manual*, Cold Spring Harbor Laboratory Press (1989); and Ausubel et al., Eds. *Current Protocols in Molecular Biology*, Wiley Interscience, New York (1987, 1993).

Many vector systems are available for the expression of cloned anti-TNF peptide H and L chain genes in mammalian cells (see Glover, Ed., *DNA Cloning*, Vol. II, pp. 143–238, IRL Press, Washington, D.C., 1985). Different approaches can be followed to obtain complete H2L2 antibodies. It is possible to co-express H and L chains in the same cells to achieve intracellular association and linkage of H and L chains into complete tetrameric H2L2 antibodies. The co-expression can occur by using either the same or different plasmids in the same host. Genes for both H and L chains can be placed into the same plasmid, which is then transfected into cells, thereby selecting directly for cells that express both chains. Alternatively, cells can be transfected first with a plasmid encoding one chain, for example the L chain, followed by transfection of the resulting cell line with an H chain plasmid containing a second selectable marker. Cell lines producing H2L2 molecules via either route could be transfected with plasmids encoding additional copies of peptides, H, L, or H plus L chains in conjunction with additional selectable markers to generate cell lines with enhanced properties, such as higher production of assembled H2L2 antibody molecules or enhanced stability of the transfected cell lines.

Receptor Molecules

Receptor molecules (also referred to herein as soluble TNF receptors) useful in the methods and compositions of the present invention are those that bind TNF with high affinity (see, e.g., Feldmann et al., International Publication No. WO 92/07076 published Apr. 30, 1992), incorporated herein by reference) and possess low immunogenicity. In particular, the 55 kDa (p55 TNF-R) and the 75 kDa (p75 TNF-R) TNF cell surface receptors are useful in the present invention. Truncated forms of these receptors, comprising the extracellular domains (ECD) of the receptors or functional portions thereof, are also useful in the present invention. Truncated forms of the TNF receptors, comprising the ECD, have been detected in urine and serum as 30 kDa and 40 kDa TNF inhibitory binding proteins (Engelmann, H. et al., *J. Biol. Chem.* 265:1531–1536 (1990)). TNF receptor multimeric molecules and TNF immunoreceptor fusion molecules, and derivatives and fragments or portions thereof, are additional examples of receptor molecules which are useful in the methods and compositions of the present invention. The receptor molecules which can be used in the invention are characterized by their ability to treat patients for extended periods with good to excellent alleviation of symptoms and low toxicity. Low immunogenicity and/or high affinity, as well as other undefined properties, may contribute to the therapeutic results achieved.

TNF receptor multimeric molecules useful in the present invention comprise all or a functional portion of the ECD of two or more TNF receptors linked via one or more polypeptide linkers. The multimeric molecules can further comprise a signal peptide of a secreted protein to direct expression of the multimeric molecule. These multimeric molecules and methods for their production have been described in U.S. application Ser. No. 08/437,533 (filed May 9, 1995), the content of which is entirely incorporated herein by reference.

TNF immunoreceptor fusion molecules useful in the methods and compositions of the present invention comprise at least one portion of one or more immunoglobulin molecules and all or a functional portion of one or more TNF receptors. These immunoreceptor fusion molecules can be assembled as monomers, or hetero- or homo-multimers. The immunoreceptor fusion molecules can also be monovalent or multivalent. An example of such a TNF immunoreceptor fusion molecule is TNF receptor/IgG fusion protein.

TNF immunoreceptor fusion molecules and methods for their production have been described in the art (Lesslauer et al., i Eur. J. Immunol. 21:2883–2886 (1991); Ashkenazi et al., *Proc. Natl. Acad. Sci. USA* 88:10535–10539 (1991); Peppel et al., *J. Exp. Med.* 174:1483–1489 (1991); Kolls et al., *Proc. Natl. Acad. Sci. USA* 91:215–219 (1994); Butler et al., *Cytokine* 6(6):616–623 (1994); Baker et al., *Eur. J. Immunol.* 24:2040–2048 (1994); Beutler et al., U.S. Pat. No. 5,447,851; and U.S. application Ser. No. 08/442,133 (filed May 16, 1995)). These references are entirely incorporated herein by reference. Methods for producing immunoreceptor fusion molecules can also be found in Capon et al., U.S. Pat. No. 5,116,964; Capon et al., U.S. Pat. No. 5,225,538; and Capon et al., *Nature* 337:525–531 (1989), which references are entirely incorporated herein by reference.

Derivatives, fragments, regions and functional portions of the receptor molecules functionally resemble the receptor molecules that can be used in the present invention (i.e., they bind TNF with high affinity and possess low immunogenicity). A functional equivalent or derivative of the receptor molecule refers to the portion of the receptor molecule, or the portion of the receptor molecule sequence which encodes the receptor molecule, that is of sufficient size and sequences to functionally resemble the receptor molecules that can be used in the present invention (i.e., bind TNF with high affinity and possess low immunogenicity). A functional equivalent of the receptor molecule also includes modified receptor molecules that functionally resemble the receptor molecules that can be used in the present invention (i.e., bind TNF with high affinity and possess low immunogenicity). For example, a functional equivalent of the receptor molecule can contain a "SILENT" codon or one or more amino acid substitutions, deletions or additions (e.g., substitution of one acidic amino acid for another acidic amino acid; or substitution of one codon encoding the same or different hydrophobic amino acid for another codon encoding a hydrophobic amino acid). See Ausubel et al., *Current Protocols in Molecular Biology*, Greene Publishing Assoc. and Wiley-Interscience, New York (1989).

CD4+ T Cell Inhibiting Agents

As used herein, a "CD4+ T cell inhibiting agent" decreases, blocks, inhibits, abrogates or interferes with the activation of CD4+ T cells or the interaction of CD4+ T cells with antigen presenting cells (APC). CD4+ T cell inhibiting agents include antibodies to T cells or to their receptors, such as anti-CD4, anti-CD28, anti-CD52 (e.g., CAMPATH-1H) and anti-IL-2R antibodies; antibodies to APC or to their receptors, such as anti-class II, anti-ICAM-1, anti-LFA-3, and anti-LFA-1 antibodies; peptides and small molecules blocking the T cell/APC interaction, including those which block the HLA class II groove, CD4 or block signal transduction in T-cell activation, such as cyclosporin and cyclosporin analogs, particularly cyclosporin A, or FK-506, and antibodies to B cells including CD5+ B cells, such as CD19, CD20, CD21, CD23 and BB/7 or B1 antibodies, ligands for CD28, and inhibitors of B7/CD28, such as CTLA4-Ig. B cells, including CD5+ B cells, are considered to be an important type of APC in disease processes (Plater-Zyberk et al., *Ann. N.Y. Acad. Sci.* 651:540–555 (1992)), and thus, anti-B cell antibodies can be particularly useful in the methods and compositions of the present invention.

Anti-CD4 Antibodies

Anti-CD4 antibodies useful in the present invention include polyclonal, monoclonal, chimeric, humanized, resurfaced and recombinant antibodies and fragments thereof which are characterized by high affinity binding to CD4 and low toxicity (including HAMA and/or HACA response). In particular, an antibody where the individual components, such as the variable region, constant region and framework, individually and/or collectively possess low immunogenicity is useful in the present invention. The antibodies which can be used in the invention are characterized by their ability to treat patients for extended periods with good to excellent alleviation of symptoms and low toxicity. Low immunogenicity and/or high affinity, as well as other undefined properties, may contribute to the therapeutic results achieved.

Techniques described herein for producing anti-TNF antibodies can be employed in producing anti-CD4 antibodies that can be used in the present invention.

Monoclonal antibodies reactive with CD4 can be produced using somatic cell hybridization techniques (Kohler and Milstein, *Nature* 256: 495–497 (1975)) or other techniques. In a typical hybridization procedure, a crude or purified protein or peptide comprising at least a portion of CD4 can be used as the immunogen. An animal is vaccinated with the immunogen to obtain anti-CD4 antibody-producing spleen cells. The species of animal immunized will vary depending on the species of monoclonal antibody desired. The antibody producing cell is fused with an immortalizing cell (e.g., myeloma cell) to create a hybridoma capable of secreting anti-CD4 antibodies. The unfused residual antibody-producing cells and immortalizing cells are eliminated. Hybridomas producing desired antibodies are selected using conventional techniques and the selected hybridomas are cloned and cultured.

Polyclonal antibodies can be prepared by immunizing an animal with a crude or purified protein or peptide comprising at least a portion of CD4. The animal is maintained under conditions whereby antibodies reactive with either CD4 are produced. Blood is collected from the animal upon reaching a desired titre of antibodies. The serum containing the polyclonal antibodies (antisera) is separated from the other blood components. The polyclonal antibody-containing serum can optionally be further separated into fractions of particular types of antibodies (e.g., IgG, IgM).

Examples of anti-CD4 antibodies that can be used in the present invention are described in the art (see, e.g., U.S. application Ser. No. 07/867,100 (filed Jun. 25, 1992); Grayheb et al., *J. Autoimmunity* 2:627–642 (1989); Ranges et al, *J. Exp. Med.* 162: 1105–1110 (1985); Hom et al., *Eur. J. Immunol.* 18: 881–888 (1988); Wooley et al., *J. Immunol.* 134: 2366–2374 (1985); Cooper et al., *J. Immunol* 141: 1958–1962 (1988); Van den Broek et al., *Eur. J. Immunol.* 22: 57–61 (1992); Wofsy et al., *J. Immunol.* 134: 852–857 (1985); Wofsy et al., *J. Immunol.* 136: 4554–4560 (1986); Ermak et al., *Laboratory Investigation* 61: 447–456 (1989); Reiter et al., 34:525–532 (1991); Herzog et al., *J. Autoimmun.* 2:627 (1989); Ouyang et al., *Dig. Dis. Sci.* 33:1528–1536 (1988); Herzog et al., *Lancet ii:* 1461 (Dec. 19, 1987); Emmrich et al., *Lancet* 338:570–571 (1991), which references are entirely incorporated herein by reference).

Administration

TNF antagonists, CD4+ T cell inhibiting agents, and the compositions of the present invention can be administered to an individual in a variety of ways. The routes of administration include intradermal, transdermal (e.g., in slow release polymers), intramuscular, intraperitoneal, intravenous, including infusion and/or bolus injection, subcutaneous, oral, topical, epidural, buccal, rectal, vaginal and intranasal routes. Other suitable routes of administration can also be used, for example, to achieve absorption through epithelial or mucocutaneous linings. TNF antagonists, CD4+ T cell inhibiting agents, and the compositions of the present invention can also be administered by gene therapy wherein a DNA molecule encoding the therapeutic protein or peptide is administered to the patient, e.g., via a vector, which causes the protein or peptide to be expressed and secreted at therapeutic levels in vivo. In addition, the TNF antagonists, CD4+ T cell inhibiting agents and compositions of the present invention can be administered together with other components of biologically active agents, such as pharmaceutically acceptable surfactants (e.g., glycerides), excipients (e.g., lactose), carriers, diluents and vehicles. If desired, certain sweetening, flavoring and/or coloring agents can also be added.

The TNF antagonists and CD4+ T cell inhibiting agents can be administered prophylactically or therapeutically to an individual. TNF antagonists can be administered prior to, simultaneously with (in the same or different compositions) or sequentially with the administration of a CD4+ T cell inhibiting agent.

For parenteral (e.g., intravenous, subcutaneous, intramuscular) administration, TNF antagonists, CD4+ T cell inhibiting agents and the compositions of the present invention can be formulated as a solution, suspension, emulsion or lyophilized powder in association with a pharmaceutically acceptable parenteral vehicle. Examples of such vehicles are water, saline, Ringer's solution, dextrose solution, and 5% human serum albumin. Liposomes and nonaqueous vehicles such as fixed oils can also be used. The vehicle or lyophilized powder can contain additives that maintain isotonicity (e.g., sodium chloride, mannitol) and chemical stability (e.g., buffers and preservatives). The formulation is sterilized by commonly used techniques.

Suitable pharmaceutical carriers are described in Remington's Pharmaceutical Sciences, A. Osol, a standard reference in this field of art.

For example, a parenteral composition suitable for administration by injection is prepared by dissolving 1.5% by weight of active ingredient in 0.9% sodium chloride solution.

In a particular embodiment, cyclosporin and cyclosporin analogs can be administered to an individual orally or intravenously. However, other therapeutically efficacious routes of administration can also be used, such as those described above. Cyclosporin, or a cyclosporin analog, can be administered alone, but is generally administered with a pharmaceutical carrier selected on the basis of the chosen route of administration and standard pharmaceutical practice. Presently available oral and intravenous formulations of cyclosporin include SANDIMMUNE® soft gelatin capsules, oral solution and injection (Sandoz Pharmaceuticals/Consumer Division, East Hanover, N.J.).

TNF antagonists and CD4+ T cell inhibiting agents are co-administered in therapeutically effective amounts; the compositions of the present invention are administered in a therapeutically effective amount. As used herein, a "therapeutically effective amount" is such that co-administration of TNF antagonist and CD4+ T cell inhibiting agent, or administration of a composition of the present invention, results in inhibition of the biological activity of TNF relative to the biological activity of TNF when therapeutically effective amounts of TNF antagonist and CD4+ T cell inhibiting agent are not co-administered, or relative to the biological activity of TNF when a therapeutically effective amount of the composition is not administered. A therapeutically effective amount is that amount of TNF antagonist and CD4+ T cell inhibiting agent necessary to significantly reduce or eliminate symptoms associated with a particular TNF-mediated disease. As used herein, a therapeutically effective amount is not an amount such that administration of the TNF antagonist alone, or administration of the CD4+ T cell inhibiting agent alone, must necessarily result in inhibition of the biological activity of TNF or in immunosuppressive activity.

Once a therapeutically effective amount has been administered, a maintenance amount of TNF antagonist alone, of CD4+ T cell inhibiting agent alone, or of a combination of TNF antagonist and CD4+ T cell inhibiting agent can be administered to the individual. A maintenance amount is the amount of TNF antagonist, CD4+ T cell inhibiting agent, or combination of TNF antagonist and CD4+ T cell inhibiting agent necessary to maintain the reduction or elimination of symptoms achieved by the therapeutically effective dose. The maintenance amount can be administered in the form of a single dose, or a series or doses separated by intervals of days or weeks.

The dosage administered to an individual will vary depending upon a variety of factors, including the pharmacodynamic characteristics of the particular antagonists, and its mode and route of administration; size, age, health, sex, body weight and diet of the recipient; nature and extent of symptoms of the disease being treated, kind of concurrent treatment, frequency of treatment, and the effect desired. In vitro and in vivo methods of determining the inhibition of TNF in an individual are well known to those of skill in the art. Such in vitro assays can include a TNF cytotoxicity assay (e.g., the WEHI assay or a radioimmunoassay, ELISA). In vivo methods can include rodent lethality assays and/or primate pathology model systems (Mathison et al., *J. Clin. Invest.* 81: 1925–1937 (1988); Beutler et al., *Science* 229: 869–871 (1985); Tracey et al., *Nature* 330: 662–664 (1987); Shimamoto et al., *Immunol. Lett.* 17: 311–318 (1988); Silva et al., *J. Infect. Dis.* 162: 421–427 (1990); Opal et al., *J. Infect. Dis.* 161: 1148–1152 (1990); Hinshaw et al., *Circ. Shock* 30: 279–292 (1990)).

TNF antagonists and CD4+ T cell inhibiting agents can be co-administered in single or multiple doses depending upon factors such as nature and extent of symptoms, kind of concurrent treatment and the effect desired. Thus, other therapeutic regimens or agents (e.g., multiple drug regimens) can be used in combination with the therapeutic co-administration of TNF antagonists and CD4+ T cell inhibiting agents. Adjustment and manipulation of established dosage ranges are well within the ability of those skilled in the art.

In a particular embodiment, TNF antagonist and cyclosporin (or cyclosporin analog) can be co-administered in single or multiple doses depending upon factors such as nature and extent of symptoms, kind of concurrent treatment and the effect desired. Other therapeutic regimens or agents (e.g., multiple drug regimens) can be used in combination with the therapeutic co-administration of TNF antagonists and cyclosporin (or cyclosporin analog). Adjustment and manipulation of established dosage ranges are well within the ability of those skilled in the art.

Usually a daily dosage of active ingredient can be about 0.01 to 100 milligrams per kilogram of body weight. Ordinarily 1 to 40 milligrams per kilogram per day given in divided doses 1 to 6 times a day or in sustained release form is effective to obtain desired results. Second or subsequent administrations can be administered at a dosage which is the same, less than or greater than the initial or previous dose administered to the individual.

A second or subsequent administration is preferably during or immediately prior to relapse or a flare-up of the disease or symptoms of the disease. For example, the second and subsequent administrations can be given between about one day to 30 weeks from the previous administration. Two, three, four or more total administrations can be delivered to the individual, as needed.

Dosage forms (composition) suitable for internal administration generally contain from about 0.1 milligram to about 500 milligrams of active ingredient per unit. In these pharmaceutical compositions the active ingredient will ordinarily be present in an amount of about 0.5–95% by weight based on the total weight of the composition.

The present invention will now be illustrated by the following examples, which are not intended to be limiting in any way.

EXAMPLES

Example 1

Treatment of Induced Arthritis in a Murine Model Using Anti-CD4 Antibody and Anti-TNF Antibody The murine model of collagen type II induced arthritis has similarities to rheumatoid arthritis (RA) in its marked MHC class II predisposition, as well as in histology, immunohistology, and erosions of cartilage and bone. Furthermore, there is a good correlation of therapeutic response with human rheumatoid arthritis. For example, in both diseases anti-TNF antibody has beneficial effects (Williams, R. O. et al., *Proc. Natl. Acad. Sci. USA* 89:9784–9788 (1992); Elliott, M. J. et al., *Arthritis & Rheumatism* 36:1681–1690 (1993)), and anti-CD4 antibody has minimal effect in mouse arthritis as well as in human arthritis (Williams, R. O. et al., *Proc. Natl. Acad. Sci. USA* 91:2762–2766 (1994) Horneff, G. et al., *Arthritis & Rheumatism* 34:129–140 (1991)). Thus, the animal model serves as a good approximation to human disease.

The model of rheumatoid arthritis used herein, i.e., the collagen type II induced arthritis in the DBA/1 mouse, is described by Williams, R. O. et al. (*Proc. Natl. Acad. Sci. USA* 89:9784–9788 (1992)). Type II collagen was purified from bovine articular cartilage by limited pepsin solubilization and salt fractionation as described by Miller (*Biochemistry* 11:4903–4909 (1972)).

Experimental Procedure

Male DBA/1 mice were immunized intradermally at 8–12 weeks of age with 100 μg type II collagen emulsified in Freund's complete adjuvant (Difco Laboratories, East Molsey, UK). Day one of arthritis was considered to be the day that erythema and/or swelling was first observed in one or more limbs. Arthritis became clinically evident around 30 days after immunization with type II collagen. For each mouse, treatment was started on the first day that arthritis was observed and continued over a 10 day period, after which the mice were sacrificed and joints were processed for histology. Monoclonal antibody (mAb) treatment was administered on days 1, 4, and 7. For anti-TNF antibody, TN3-19.12, a neutralizing hamster IgG1 anti-TNFα/β monoclonal antibody (mAb), was used (Sheehan, K. C. et al., *J. Immunology* 142:3884–3893 (1989)). The isotype control was L2. The anti-TNF antibody and the isotype control were provided by R. Schreiber, Washington University Medical School (St. Louis, Mo., USA), in conjunction with Celltech (Slough, UK). The cell-depleting anti-CD4 monoclonal antibody (rat IgG2b) consisted of a 1:1 mixture of YTS 191.1.2 and YTA 3.1.2, provided by H. Waldmann (University of Cambridge, UK) (Galfre, G. et al., *Nature* 277: 131–133 (1979); Cobbold, S. P. et al., *Nature* 312: 548–551 (1984); Qin, S. et al., *European J. Immunology* 17:1159–1165 (1987)).

Paw-swelling

First, a sub-optimal dose of 50 μg of anti-TNF antibody alone was compared with the same dose given together with 200 μg of anti-CD4 antibody. To verify the results, two separate but identical experiments were carried out (18–19 mice/group). Paw-swelling was monitored for 10 days by measuring the thickness of each affected hind paw with calipers. Neither anti-CD4 antibody alone nor sub-optimal anti-TNF antibody alone were able to significantly reduce paw-swelling (FIG. 1). However, treatment with anti-TNF antibody and anti-CD4 antibody resulted in a consistently and statistically significant reduction in paw-swelling relative to the group given control mAb (P<0.01). Furthermore, in both experiments, combined anti-TNF/anti-CD4 antibody treatment (also referred to herein as anti-CD4/TNF antibody treatment) produced a significant reduction in paw-swelling relative to anti-CD4 antibody alone (P<0.05), and anti-TNF antibody alone (P<0.05).

Figure 2:
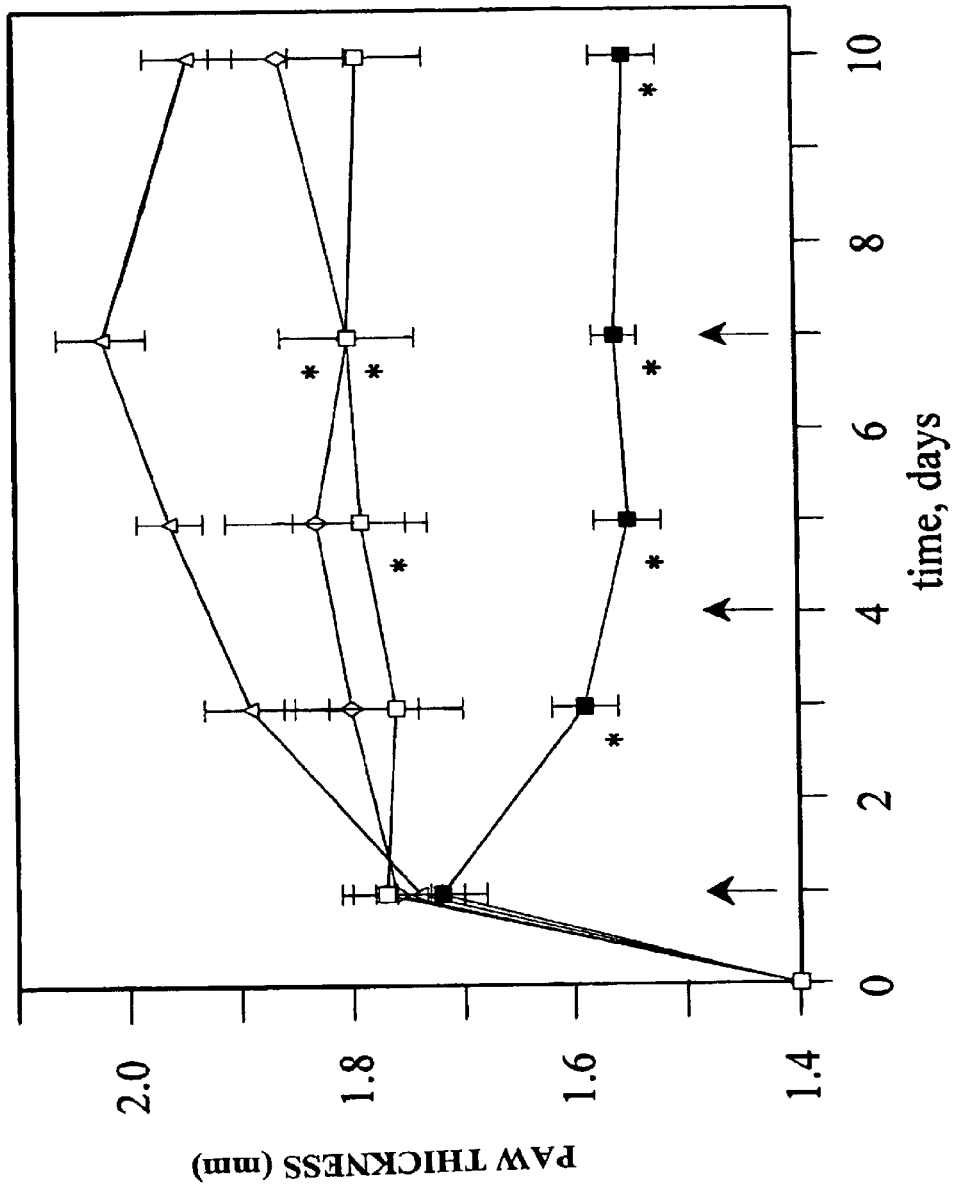
FIG. 2 is a graph showing the effect of administering an optimal dose (300 μg) of anti-TNF antibody alone and in combination with anti-CD4 antibody (200 μg) to male DBA/1 mice on the suppression of arthritis as assessed by paw-swelling measurements. Triangle=control antibody; diamond=anti-CD4 antibody; open square=anti-TNF antibody; closed square=anti-CD4 antibody plus anti-TNF antibody. An asterisk indicates a significant reduction compared to the group of mice administered control antibody (P<0.05; two-sample t test). Arrows indicate times of injection.

Next, an optimal dose of anti-TNF antibody (300 μg) alone was compared in two separate but identical experiments (11–13 mice/group) with the same dose given in combination with anti-CD4 antibody. As before, the combined anti-TNF/anti-CD4 antibody treatment resulted in a significant reduction in paw-swelling compared to treatment with the control mAb (P<0.01; FIG. 2). In addition, paw swelling was significantly reduced in the combined anti-CD4/anti-TNF antibody treated group relative 25 to the groups administered anti-CD4 antibody alone (P<0.01) or anti-TNF antibody alone (P<0.01). A reduction in paw swelling was also observed in the mice administered anti-CD4 antibody alone and in the mice administered anti-TNF antibody alone. The reduction in paw swelling attributable to anti-TNF antibody treatment was broadly comparable with previously published findings in which treatment with TN3-19.12 (300 μg/mouse) resulted in a mean reduction in paw-swelling over the treatment period of around 34% relative to controls (Williams, R. O. et al., *Proc. Natl. Acad. Sci. USA* 89:9784–9788 (1992)).

Limb Involvement

In collagen-induced arthritis, as in RA, it is usual for additional limbs to become involved after the initial appearance of clinical disease and new limb involvement is an important indicator of the progression of the disease. To determine the effect of anti-CD4/anti-TNF antibody treatment on new limb involvement, the number of limbs with clinically detectable arthritis at the end of the 10 day treatment period was compared with the number of arthritic limbs before treatment. In mice given the control mAb there was an increase in limb involvement over the 10 day period of approximately 50%. Results are shown in Table 1.

TABLE 1

Combined anti-CD4/anti-TNF Antibody Inhibits Progression of Clinical Arthritis

| | Number of Limbs Affected | | |
|---|---|---|---|
| | (Mean ± SEM) | | Increase |
| Treatment | Day 1 | Day 10 | (%) |
| Sub-optimal anti-TNF (50 µg) | | | |
| anti-CD4 (n = 18) | 1.30 ± 0.10 | 1.90 ± 0.12 | 46.1 |
| anti-TNF (n = 19) | 1.20 ± 0.09 | 1.65 ± 0.17 | 37.5 |
| anti-CD4/TNF (n = 18) | 1.40 ± 0.17 | 1.45 ± 0.22 | 3.4[1] |
| control mAb (n = 18) | 1.43 ± 0.15 | 2.24 ± 0.18 | 56.6 |
| Optimal anti-TNF (300 µg) | | | |
| anti-CD4 (n = 12) | 1.27 ± 0.10 | 1.80 ± 0.14 | 42.0 |
| anti-TNF (n = 11) | 1.50 ± 0.17 | 1.64 ± 0.20 | 9.52 |
| anti-CD4/TNF (n = 13) | 1.25 ± 0.11 | 1.25 ± 0.11 | 0[3] |
| control mAb (n = 12) | 1.53 ± 0.19 | 2.27 ± 0.25 | 47.8 |

[1]$P < 0.05$ (anti-CD4/TNF antibodies vs. control mAb)
[2]$P < 0.05$ (anti-TNF antibodies vs. control mAb)
[3]$P < 0.005$ (anti-CD4/TNF antibodies vs. control mAb)

There was some reduction in new limb involvement in the groups given anti-CD4 antibody alone and sub-optimal anti-TNF antibody alone, although the differences were not significant. In the group given optimal anti-TNF antibody, the increase in limb involvement was less than 10% ($P<0.05$). More striking, however, was the almost complete absence of new limb involvement in the groups given combined anti-CD4/anti-TNF antibodies. Thus, the increase in new limb involvement was only 3% in mice given anti-CD4 antibody plus suboptimal anti-TNF antibody ($P<0.05$) and 0% in mice given anti-CD4 antibody plus optimal anti-TNF antibody ($P<0.005$).

Histology

After 10 days, the mice were sacrificed; the first limb that had shown clinical evidence of arthritis was removed from each mouse, formalin-fixed, decalcified, and wax-embedded before sectioning and staining with haematoxylon and eosin. A sagittal section of the proximal interphalangeal (PIP) joint of the middle digit was studied in a blind fashion for the presence or absence of erosions in either cartilage or bone (defined as demarcated defects in cartilage or bone filled with inflammatory tissue). The comparisons were made only between the same joints, and the arthritis was of identical duration. Erosions were observed in almost 100% of the PIP joints from the control groups and in approximately 70–80% of the joints given either anti-CD4 antibody alone or sub-optimal anti-TNF antibody alone. Results are shown in Table 2.

TABLE 2

Proportions of PIP Joints Showing Significant Erosion of Cartilage and/or Bone

| Treatment | Joints with Erosions |
|---|---|
| Sub-optimal anti-TNF (50 µg) | |
| anti-CD4 | 13/18 (72%) |
| anti-TNF | 14/19 (74%) |
| anti-CD4/TNF | 4/18 (22%)[1] |
| control mAb | 17/18 (94%) |
| Optimal anti-TNF (300 µg) | |
| anti-CD4 | 10/12 (83%) |
| anti-TNF | 6/11 (54%)[2] |
| anti-CD4/TNF | 4/13 (31%)[3] |
| control mAb | 12/12 (100%) |

[1]$P < 0.01$ (anti-CD4/TNF antibodies vs. anti-CD4 antibody alone; anti-TNF antibody alone and control mAb)
[2]$P < 0.01$ (anti-TNF antibody alone vs. control mAb)
[3]$P < 0.01$ (anti-CD4/TNF antibodies vs. anti-CD4 antibody alone and control mAb)

An optimal dose of anti-TNF antibody alone significantly reduced pathology, as reported previously (Williams, R. O. et al., *Proc. Natl. Acad. Sci. USA* 89: 9784–9788 (1992)). Thus, in the mice given optimal anti-TNF antibody alone the proportion of joints showing erosive changes was reduced to 54% ($P<0.001$) whereas in the groups given anti-CD4 antibody plus either sub-optimal or optimal anti-TNF antibody, only 22% ($P<0.01$) and 31% ($P<0.01$) of the joints, respectively, were eroded. Thus, 300 µg of anti-TNF antibody alone gave a degree of protection against joint erosion but combined anti-CD4/anti-TNF antibodies provided significantly greater protection.

Depletion of CD4+ T Cells

The extent to which anti-CD4 antibody treatment depleted peripheral CD4+ T cells was determined by flow cytometry. To enumerate the proportion of CD4+ lymphocytes in disassociated spleen populations or peripheral blood, cells were incubated with phycoerythrin-conjugated anti-CD4 (Becton Dickinson, Oxford, UK), then analyzed by flow cytometry using a flow cytometer sold under the trademark "FACScan" (Becton Dickinson) with scatter gates set on the lymphocyte fraction. Anti-CD4 antibody treatment resulted in 98% (±1%) depletion of CD4+ T cells in the spleen and 96% (±3%) depletion of CD4+ T cells in the blood.

Immunohistochemistry

The possible persistence of CD4+ T cells in the joint despite virtual elimination of peripheral CD4+ T cells was next investigated by immunohistochemical analysis of sections from treated arthritic mice. Wax-embedded sections were de-waxed, trypsin digested, then incubated with anti-CD4 mAb (YTS 191.1.2/YTA 3.1.2). To confirm the T cell identity of the CD4+ T cells, sequential sections were stained with anti-Thy-1 mAb (YTS 154.7) (Cobbold, S. P. et al., *Nature* 312:548–551 (1984)). Control sections were incubated with HRPN11/12a (an isotype control mAb; a gift from Stephen Hobbs, Institute of Cancer Research, London). Detection of bound antibody was by alkaline phosphatase/rat anti-alkaline phosphatase complex (APAAP; Dako, High Wycombe, UK) and fast red substrate as described (Deleuran, B. W. et al., *Arthritis & Rheumatism* 34:1125–1132(1991)). Small numbers of CD4+ T cells were detected in the joints, not only of mice given control mAb, but also of those treated with anti-CD4 antibody. Furthermore, within the small number of mice that were studied (four per treatment group), it was not possible to detect significantly reduced numbers of CD4+ T cells in the groups given anti-CD4 antibody alone or anti-CD4 antibody plus anti-TNF antibody. Anti-CD4 antibody treatment did not, therefore, eliminate CD4+ T cells from the joint.

Anti-Collagen IgG Levels

Serum anti-collagen IgG levels were measured by enzyme-linked immunosorbent assay (ELISA). Microtitre plates were coated with bovine type II collagen (2 μg /ml), blocked, then incubated with test sera in serial dilution steps. Detection of bound IgG was by incubation with alkaline phosphatase-conjugated goat anti-mouse IgG, followed by substrate (dinitrophenol phosphate). Optical densities were read at 405 nm. A reference sample, consisting of affinity-purified mouse anti-type II collagen antibody, was included on each plate. Results are shown in Table 3.

TABLE 3

Serum Levels of Anti-type II collagen IgG

| Treatment | Anti-collagen IgG (Mean ± SEM) (μg/ml) |
|---|---|
| Sub-optimal anti-TNF (50 μg) | |
| anti-CD4 (n = 18) | 285 ± 37 |
| anti-TNF (n = 19) | 208 ± 29 |
| anti-CD4/TNF (n = 18) | 208 ± 34 |
| control mAb (n = 18) | 238 ± 36 |
| Optimal anti-TNF (300 μg) | |
| anti-CD4 (n = 12) | 288 ± 39 |
| anti-TNF (n = 11) | 315 ± 49 |
| anti-CD4/TNF (n = 13) | 203 ± 33 |
| control mAb (n = 12) | 262 ± 47 |

Serum levels of anti-type II collagen IgG were not significantly altered within the 10 day treatment period by anti-CD4 antibody alone, anti-TNF antibody alone, or anti-CD4 antibody plus anti-TNF antibody.

Anti-Globulin Response

To find out whether anti-CD4 antibody treatment prevented a neutralizing anti-globulin response against the anti-TNF mAb, IgM anti-TN3-19.12 levels on day 10, as measured by ELISA, were compared. At this time, an IgG anti-TN3-19.12 response was not detected. Microtitre plates were coated with TN3-19.12 (5 μg /ml), blocked, then incubated with serially diluted test sera. Bound IgM was detected by goat anti-mouse IgM-alkaline phosphatase conjugate, followed by substrate. The results demonstrated that anti-CD4 antibody was highly effective in preventing the development of an anti-TN3-19.12 antibody response (Table 4). Next, to determine whether anti-CD4 antibody treatment led to increased levels of circulating TNFα (by reducing the antibody response to the hamster anti-TNF antibody), an ELISA was carried out in which recombinant murine TNFα was used to detect free TN3-19.12 in the sera of mice on day 10 of the experiment. Microtitre plates were coated with recombinant murine TNFα (Genentech Inc., South San Francisco, Calif.), blocked, then incubated with test sera. Goat anti-hamster IgG-alkaline phosphatase conjugate (adsorbed against murine IgG) was then applied, followed by substrate. Quantitation was by reference to a sample of known concentration of TN3-19.12. Results are shown in Table 4.

TABLE 4

IgM anti-TN3 Titres and Levels of Unbound TN3

| Treatment | Reciprocal of Anti-TN3 Titre (Mean) | Unbound TN3 (Mean ± SEM) (μg/ml) |
|---|---|---|
| Sub-optimal anti-TNF (50 μg) | | |
| anti-TNF (n = 12) | 242 | 8.6 ± 2.0 |
| anti-CD4/TNF (n = 12) | 84[1] | 12.1 ± 1.9 |

TABLE 4-continued

IgM anti-TN3 Titres and Levels of Unbound TN3

| Treatment | Reciprocal of Anti-TN3 Titre (Mean) | Unbound TN3 (Mean ± SEM) (μg/ml) |
|---|---|---|
| Optimal anti-TNF (300 μg) | | |
| anti-TNF (n = 12) | 528 | 90.7 ± 11.9 |
| anti-CD4/TNF (n = 2) | 91[1] | 102.7 ± 12.5 |

[1]Significantly reduced anti-TN3 titre (P < 0.005; Mann-Whitney test)

Levels of TN3-19.12 were slightly elevated in the groups given anti-CD4 antibody plus anti-TNF antibody compared to anti-TNF antibody alone, although the differences were not significantly different.

Example 2

Treatment of Induced Arthritis in a Murine Model Using TNF Receptor/IgG Fusion Protein with Anti-CD4 Antibody The murine model of collagen type II induced arthritis, described above, was used to investigate the efficacy of a human p55 TNF receptor/IgG fusion protein, in conjunction with anti-CD4 monoclonal antibody (mAb), for its ability to modulate the severity of joint disease in collagen-induced arthritis. First, a comparison was made between the efficacy of TNF receptor/IgG fusion protein treatment, anti-TNF mAb treatment, and high dose corticosteroid therapy. Subsequently, therapy with TNF receptor/IgG fusion protein in conjunction with anti-CD4 antibody was investigated.

A. Experimental Procedure

Male DBA/1 mice were immunized intradermally with 100 μg of bovine type II collagen emulsified in complete Freund's adjuvant (Difco Laboratories, East Molsey, UK). The mean day of onset of arthritis was approximately one month after immunization. After the onset of clinically evident arthritis (erythema and/or swelling), mice were injected intraperitoneally with therapeutic agents. Arthritis was monitored for clinical score and paw swelling (measured with calipers) for 10 days, after which the mice were sacrificed and joints were processed for histology. Sera were collected for analysis on day 10. Therapeutic agents were administered on day 1 (onset), day 4 and day 7. The therapeutic agents included TNF receptor/IgG fusion protein (p55-sf2), anti-TNF antibody, anti-CD4 antibody, and methylprednisolone acetate.

B. Comparison of Treatment with TNF Receptor/IgG Fusion Protein, Anti-TNF Antibody, or Methylprednisolone Acetate Using the Experimental Procedure described above, groups of mice were subjected to treatment with TNF receptor/IgG protein (2 μg) (18 mice), TNF receptor/IgG protein (20 μg) (18 mice), TNF receptor/IgG protein (100 μg) (12 mice), anti-TNF monoclonal antibody (mAb) (300 μg) (17 mice), methylprednisolone acetate (6 mice), an irrelevant human IgG1 monoclonal antibody (mAb) (6 mice), or saline (control). The TNF receptor/IgG fusion protein, herein referred to as p55-sf2 was provided by Centocor, Inc., Malvern Pa. (Butler et al., *Cytokine* 6:616–623 (1994); Scallon et al., *Cytokine* 7:759–770 (1995)); it is dimeric and consists of the human p55 TNF receptor (extracellular domains) fused to a partial J sequence followed by the whole of the constant region of the human IgG1 heavy chain, itself associated with the constant region of a kappa light chain. The anti-TNF antibody was TN3-19.12, a neutralizing hamster IgG1 anti-TNFα/β monoclonal antibody (Sheehan, K. C. et al., *J. Immunology*

142:3884–3893 (1989)), and was provided by R. Schreiber, Washington University Medical School (St. Louis, Mo., USA), in conjunction with Celltech (Slough, UK). Neutralizing titres were defined as the concentration of TNFα neutralizing agent required to cause 50% inhibition of killing of WEHI 164 cells by trimeric recombinant murine TNFα; the neutralizing titre of p55-sf2 was 0.6 ng/ml, compared with 62.0 ng/ml for anti-TNF mAb (TN3-19.12), using 60 pg/ml mouse TNFα. The corticosteroid, methylprednisolone acetate (Upjohn, Crawley, UK) was administered by intraperitoneal injection as an aqueous suspension at a dosage level of 2 mg/kg body weight; using the protocol described above, this dosage is equivalent to 4.2 mg/kg/week, a dose which is higher than the typical dose used to treat refractory RA in humans (1–2 mg/kg/week).

Paw-Swelling

Treatment with p55-sf2 resulted in a dose-dependent reduction in paw-swelling over the treatment period, with the doses of 20 μg and 100 μg giving statistically significant reductions in paw-swelling relative to mice given saline ($P<0.05$). The group of mice given an irrelevant human IgG1 mAb as a control did not show any deviation from the saline-treated group, indicating that the therapeutic effects of p55-sf2 were attributable to the TNF receptor rather than the human IgG1 constant region. Similar reductions in paw-swelling were seen in mice given 300 μg of anti-TNF mAb as in those given 100 μg of p55-sf2, although anti-TNF mAb was marginally more effective than p55-sf2 at inhibiting paw-swelling. A reduction in paw-swelling was observed in the methylprednisolone acetate treated group that was comparable in magnitude to the reductions observed in the mice administered p55-sf2 at 100 μg or anti-TNF mAb at 300 μg.

Limb Involvement

The change in the number of arthritic limbs over the 10 day treatment period was examined. Results are shown in Table 5.

TABLE 5

Inhibitory Effect of TNF-Targeted Therapy on Limb Recruitment

| Treatment (number of animals) | Limbs Affected (mean ± SEM) | | Increase (%) |
|---|---|---|---|
| | Day 1 | Day 10 | |
| saline (n = 12) | 1.33 ± 0.14 | 2.25 ± 0.18 | 69% |
| p55-sf2, 2 μg (n = 18) | 1.28 ± 0.11 | 1.94 ± 0.17 | 51% |
| p55-sf2, 20 μg (n = 18) | 1.37 ± 0.11 | 1.79 ± 0.16 | 31% |
| p55-sf2, 100 μg (n = 12) | 1.17 ± 0.17 | 1.58 ± 0.23 | 35% |
| Control IgG1, 100 μg (n = 6) | 1.00 ± 0.00 | 0.15 ± 0.22 | 50% |
| Anti-TNF mAb, 300 μg (n = 17) | 1.47 ± 0.15 | 1.76 ± 0.16[1] | 20% |
| Methylprednisolone acetate (n = 6) | 1.00 ± 0.00 | 1.50 ± 0.22 | 33% |

[1] $P < 0.05$ (vs. saline; Mann Whitney Test)

A strong trend towards reduced limb recruitment was seen in the groups of mice given p55-sf2, anti-TNF mAb or methylprednisolone acetate, but only in the anti-TNF mAb treated group did the reduction reach statistical significance ($P<0.05$).

Histology

After 10 days, the mice were sacrificed; the first limb to show clinical evidence of arthritis was removed from each mouse, fixed, decalcified, wax-embedded, and sectioned and stained with haematoxylon and eosin. Sagittal sections of the proximal interphalangeal (PIP) joint of the middle digit of each mouse were studied in a blind fashion and classified according to the presence or absence of erosions, as defined above. Comparisons were thus made between identical joints, and the arthritis was of equal duration. Results are shown in Table 6.

TABLE 6

Histopathology of PIP Joints

| Treatment | PIP Joints with Erosions |
|---|---|
| Saline | 11/12 (92%) |
| p55-sf2 2 μg | 14/18 (78%) |
| p55-sf2, 20 μg | 14/18 (78%) |
| p55-sf2, 100 μg | 6/12 (50%)[1] |
| Control IgG1, 100 μg | 6/6 (100%) |
| Anti-TNF mAb, 300 μg | 7/17 (41%)[2] |
| Methylprednisolone acetate | 4/6 (67%) |

[1] $P < 0.05$ (vs. saline).
[2] $P < 0.01$ (vs. saline). Data were compared by Chi-square analysis.

Erosions were present in 92% and 100% of the PIP joints in the saline treated group and the control human IgG1 treated group, respectively. However, only 50% ($P<0.05$) of joints from the mice treated with p55-sf2 (100 μg) and 41% ($P<0.01$) of mice given anti-TNF mAb exhibited erosive changes. Some reductions in the proportion of eroded joints were observed in mice treated with 2 μg or 20 μg of p55-sf2, but these were not statistically significant. Similarly, treatment with methylprednisolone acetate did not significantly reduce joint erosion.

Anti-Collagen Antibody Levels

Anti-collagen IgG levels on day 10 were measured by ELISA as described (Williams, R. O. et al., *Proc. Natl. Acad. Sci. USA* 89: 9784–9788 (1992)). Microtitre plates were sensitized with type II collagen, then incubated with serially-diluted test sera. Bound IgG was detected using alkaline phosphatase-conjugated goat anti-mouse IgG, followed by substrate (dinitrophenol phosphate). Optical densities were read at 405 nm. No differences between any of the treatment groups were detected, suggesting that the therapeutic effect of p55-sf2 is not due to a generalized immunosuppressive effect.

C. Effect of Treatment with p55-sf2 in Conjunction with Anti-CD4 Antibody

In view of the high titres of antibodies to p55-sf2 that were detected in mice treated with the fusion protein, an experiment was carried out to determine whether concurrent administration of anti-CD4 monoclonal antibody (mAb) could enhance the therapeutic effects of p55-sf2. Using the Experimental Procedure described above, a comparison was made of three different treatment regimes: anti-CD4 mAb alone (200 μg), p55-sf2 alone (100 μg) or anti-CD4 mAb (200 μg) plus p55-sf2 (100 μg). A fourth group consisted of untreated control mice. The cell-depleting anti-CD4 mAb (rat IgG2b) consisted of a 1:1 mixture of YTS 191.1.2 and YTA 3.1.2, provided by H. Waldmann (University of Cambridge, UK) (Galfre, G. et al., *Nature* 277: 131–133 (1979); Cobbold, S. P. et al., *Nature* 312: 548–551 (1984); Qin, S. et al., *European J. Immunology* 17:1159–1165 (1987)). p55-sf2 is described above.

Paw-Swelling

Treatment with p55-sf2 alone resulted in a marked inhibition of paw-swelling, but the synergistic inhibitory effect of anti-CD4 mAb in combination with p55-sf2 was remarkable. In contrast, anti-CD4 mAb treatment alone had very little effect on paw-swelling.

Limb Involvement

As before, the progressive involvement of additional limbs following the initial appearance of arthritis was studied. Results are shown in Table 7.

TABLE 7

Anti-CD4 Antibody and p55-sf2 Prevent New Limb Recruitment

| Treatment (number of animals) | Limbs Affected (mean ± SEM) | | Increase (%) |
|---|---|---|---|
| | Day 1 | Day 10 | |
| Control (n = 6) | 1.17 ± 0.17 | 2.00 ± 0.26 | 71% |
| Anti-CD4 mAb (n = 6) | 1.17 ± 0.17 | 1.83 ± 0.31 | 56% |
| p55-sf2 (n = 7) | 1.43 ± 0.20 | 1.71 ± 0.18 | 19% |
| Anti-CD4 mAb/ p55-sf2 (n = 6) | 1.33 ± 0.21 | 1.33 ± 0.21[1] | 0% |

$P < 0.05$ (vs. controls; Mann Whitney test).

There was a mean increase in limb involvement of 71% in the control group, which was reduced to 56% in the group given anti-CD4 mAb alone, and only 19% in the group given p55-sf2. However, in the group given anti-CD4 mAb plus p55-sf2, the increase in limb involvement was 0%, a statistically significant difference.

Histology

Histological analysis of PIP joints of treated mice was carried out as described above. Results are shown in Table 8.

TABLE 8

Effects of Anti-CD4 mAb and p55-sf2 in the Prevention of Joint Erosion

| Treatment | PIP Joints with Erosions |
|---|---|
| Control | 6/6 (100%) |
| Anti-CD4 mAb | 6/6 (100%) |
| p55-sf2 | 2/6 (33%)[1] |
| Anti-CD4 mAb plus p55-sf2 | 1/6 (17%)[2] |

[1]$P = 0.06$ (vs. control)
[2]$P < 0.05$ (vs. control)

The control group and the group given anti-CD4 mAb alone gave identical results, with 6/6 (100%) of PIP joints in both groups showing significant erosions. However, in the group given p55-sf2 alone, only 2/6 (33%) of PIP joints showed erosions. Only 1/6 (17%) of joints showed erosions in the group given anti-CD4 plus p55-sf2.

Antibody Responses to p55-sf2

The IgM/IgG responses to injected p55-sf2 were measured by ELISA at the end of the treatment period (day 10). Microtitre plates were coated with p55-sf2 (5 μg/ml), blocked, then incubated with serially diluted test sera. Negative controls consisted of sera from saline-treated mice. Bound IgM or IgG were detected by the appropriate goat anti-mouse Ig-alkaline phosphatase conjugate, followed by substrate. Results are shown in Table 9.

TABLE 9

Anti-p55-sf2 Responses and Levels of Free p55-sf2 in Sera of Mice Treated with p55-sf2 Alone or in Combination with Anti-CD4 mAb

| Treatment | Anti-p55-sf2 Response (titres) | | p55-sf2 Level |
|---|---|---|---|
| | IgM | IgG | |
| Experiment 1 | | | |
| saline | 1:20 | 1:35 | — |
| p55-sf2, 2 μg | 1:50 | 1:590 | <0.2 μg/ml |
| p55-sf2, 20 μg | 1:232 | 1:3924 | <0.2 μg/ml |
| p55-sf2, 100 μg | 1:256 | 1:5280 | <0.2 μg/ml |
| Experiment 2 | | | |
| p55-sf2, 100 μg | 1:336 | 1:5100 | <0.2 μg/ml |
| p55-sf2, 100 μg, plus anti-CD4 mAb | 1:15 | 1:200 | 12.3 ± 1.1 μg/ml |

High titres of both IgM and IgG antibodies to p55-sf2 were detected in treated mice, with the highest titres being found in the mice given the 100 μg dose. These results indicate that p55-sf2, which is derived from human proteins, is highly immunogenic in mice. This may account for the slightly greater efficacy of anti-TNF mAb in vivo described in Section B above, despite the higher neutralizing titre of the fusion protein in vitro. Anti-CD4 mAb treatment was found to block almost completely the formation of both IgM and IgG antibodies to p55-sf2.

Serum Levels of Free p55-sf2

Microtitre plates were coated with recombinant murine TNFα (Genentech Inc., South San Francisco, Calif.), blocked, then incubated with test sera. Goat anti-human IgG-alkaline phosphatase conjugate was then applied followed by substrate. Quantitation was by reference to a sample of known concentration of p55-sf2.

The inhibition of the antibody response was associated with pronounced differences in the circulating levels of p55-sf2 in treated mice. Thus, free p55-sf2 was undetectable in mice given the fusion protein alone, whereas in the mice given anti-CD4 mAb plus p55-sf2, the mean serum level of p55-sf2 was 12.3 μg/ml.

Example 3
Combined Therapeutic Effect of TNF Receptor/IgG Fusion Protein and Anti-CD4 Antibody at Various Doses in the Treatment of Induced Arthritis in a Murine Model The murine model of collagen type II induced arthritis, described above, was used to investigate the efficacy of a human p55 TNF receptor/IgG fusion protein, in conjunction with anti-CD4 monoclonal antibody, for the ability to modulate the severity of joint disease in collagen-induced arthritis. A comparison was made between the efficacy of treatment with TNF receptor/IgG fusion protein in combination with anti-CD4 antibody at various dosages.

Experimental Procedure

Male DBA/1 mice were immunized intradermally with 100 μg of bovine type II collagen emulsified in complete Freund's adjuvant (Difco Laboratories, East Molsey, UK). The mean day of onset of arthritis was approximately one month after immunization. After the onset of clinically evident arthritis (erythema and/or swelling in one or more limbs), three groups of mice (6 mice per group) were subjected to treatment with one of the following therapies: 100 μg TNF receptor/IgG protein (p55-sf2; provided by Centocor, Inc., Malvern Pa.), injected intra-peritoneally on day one, or 100 μg TNF receptor/IgG protein, injected intra-peritoneally in conjunction with either 6 μg, 25 μg, 100 μg, or 400 μg anti-CD4 antibody (rat IgG2b) (1:1 mixture of YTS 191.1.2 and YTA 3.1.2; provided by H. Waldmann, University of Cambridge, UK), injected intra-peritoneally, on day one. The TNF receptor/IgG fusion protein, herein referred to as p55-sf2, and the anti-CD4 antibody are described in Example 2. Arthritis was monitored for paw-swelling (measured with calipers) for 10 days, after which the mice were sacrificed and joints were processed for histology.

Clinical Score

Clinical Score was assessed on the following scale: 0=normal; 1=slight swelling and/or erythema; 2=pronounced edematous swelling; and 3=joint rigidity. Each limb was graded, giving a maximum score of 12 per mouse.

Figure 3:
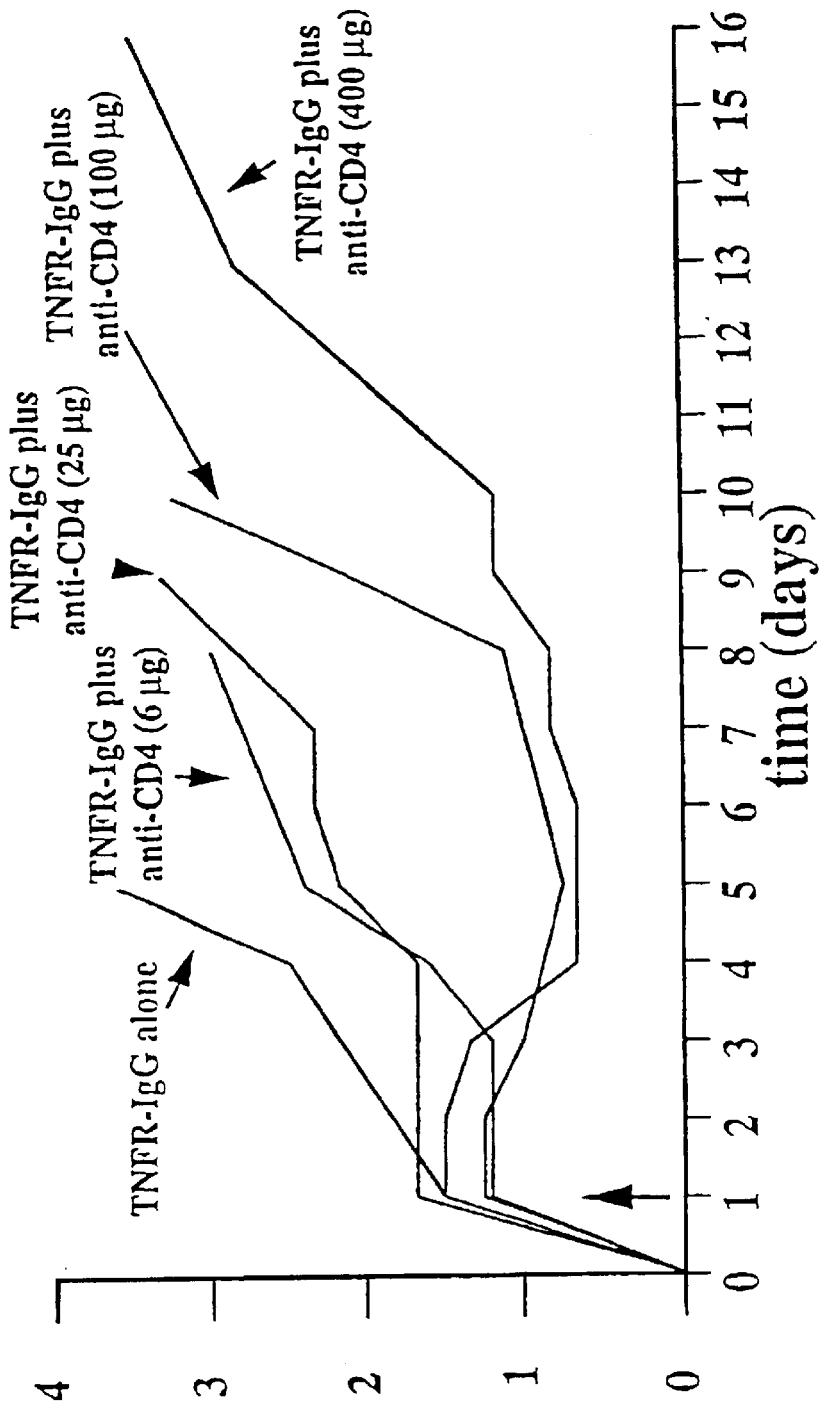
FIG. 3 is a graph showing the effect of administering 100 μg TNF receptor/IgG fusion protein alone, and a combination of 100 μg TNF receptor/IgG fusion protein plus either 6 μg, 25 μg, 100 μg or 400 μg anti-CD4 antibody to male DBA/1 mice on the suppression of arthritis as assessed by clinical score.

The results are presented in FIG. 3 and show that TNF receptor/IgG fusion protein, administered alone, reduced the severity of arthritis. However, when anti-CD4 antibody was administered in combination with TNF receptor/IgG fusion protein, greater and prolonged protection was provided. The results of this experiment also show that the duration of the synergistic ameliorative effect (therapeutic effect) between TNF receptor/IgG fusion protein and anti-CD4 antibody is dependent on the dosage of anti-CD4 antibody administered (Williams et al., *Immunology* 84:433–439 (1995)).

Example 4
Combined Therapeutic Effect of Sub-optimal Doses of Cyclosporin A and Anti-TNF Monoclonal Antibody in the Treatment of Induced Arthritis in a Murine Model The murine model of collagen type II induced arthritis, described above, was used to investigate the efficacy of co-administering a sub-optimal dose of the CD4+ T cell inhibiting agent cyclosporin A and a sub-optimal dose of anti-TNF monoclonal antibody (mAb), for the ability to modulate the severity of joint disease in collagen-induced arthritis. A comparison was made between the efficacy of treatment with a sub-optimal dose of anti-TNF antibody alone, a sub-optimal dose of CsA alone, and a combination of sub-optimal doses of CsA and anti-TNF antibody.

Experimental Procedure

Male DBA/1 mice were immunized intradermally with 100 μg of bovine type II collagen emulsified in complete Freund's adjuvant (Difco Laboratories, East Molsey, UK). The mean day of onset of arthritis was approximately one month after immunization. After the onset of clinically evident arthritis (erythema and/or swelling in one or more limbs), three groups of mice (11 mice per group) were subjected to treatment with one of the following therapies: 50 μg (2 mg/kg) L2 (the isotype control for anti-TNF antibody), injected intra-peritoneally once every three days (days 1, 4 and 7); 250 μg (10 mg/kg) cyclosporin A (SANDIMUNE®, Sandoz Pharmaceuticals, East Hanover, N.J.), injected intra-peritoneally daily; 50 μg (2 mg/kg) anti-TNF mAb TN3-19.12, injected intra-peritoneally once every three days (days 1, 4 and 7); 250 μg cyclosporin A, injected intra-peritoneally daily in conjunction with 50 μg anti-TNF mAb, injected intra-peritoneally once every three days; or phosphate-buffered saline (PBS), injected intra-peritoneally daily. The doses of CsA and anti-TNF mAb used in this experiment had in previous studies been shown to be sub-optimal, i.e., neither reagent alone had any significant effect on the severity of arthritis. Arthritis was monitored for paw swelling (measured with calipers) for 10 days, after which the mice were sacrificed and joints were processed for histology.

Paw-Swelling

Paw-swelling was monitored throughout the treatment period by measuring the thickness of each affected hind paw with calipers. The results are expressed in paw thickness (mm).

Figure 4:
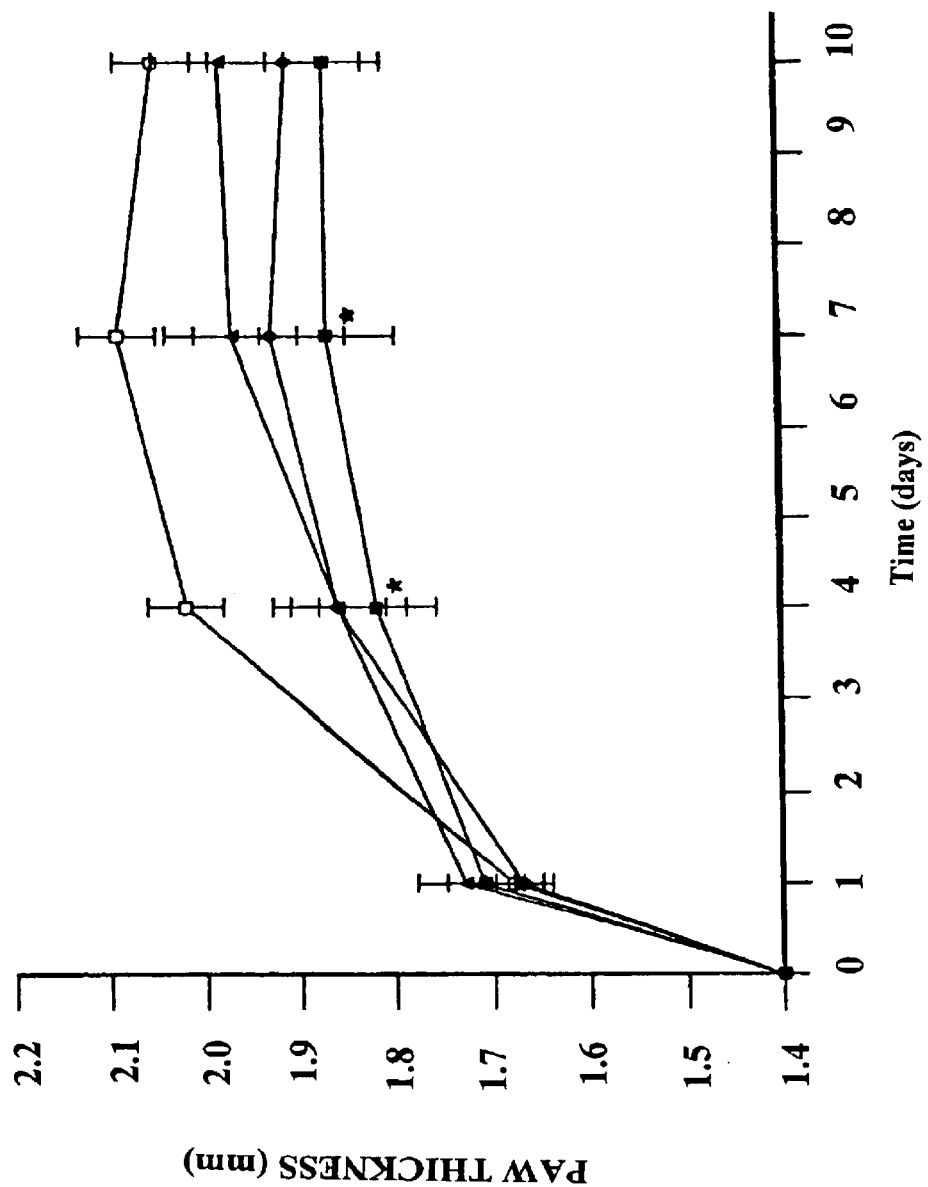
FIG. 4 is a graph showing the effect of administering 250 μg cyclosporin A, 50 μg anti-TNF antibody, and a combination of 250 μg cyclosporin A and 50 μg anti-TNF antibody to male DBA/1 mice on the suppression of arthritis as assessed by paw-swelling measurements. Open square= control; diamond=cyclosporin A; triangle=anti-TNF antibody; closed square=cyclosporin A plus anti-TNF antibody.

Treatment with a sub-optimal dose of cyclosporin A in conjunction with a sub-optimal dose of anti-TNF mAb resulted in a reduction in paw-swelling over the treatment period, relative to mice treated with control antibody. Results are shown in FIG. 4.

Clinical Score

Clinical score was assessed on the following scale: 0=normal; 1=slight swelling and/or erythema; 2=pronounced edematous swelling, and 3=joint rigidity. Each limb was graded, giving a maximum score of 12 per mouse.

Figure 5:
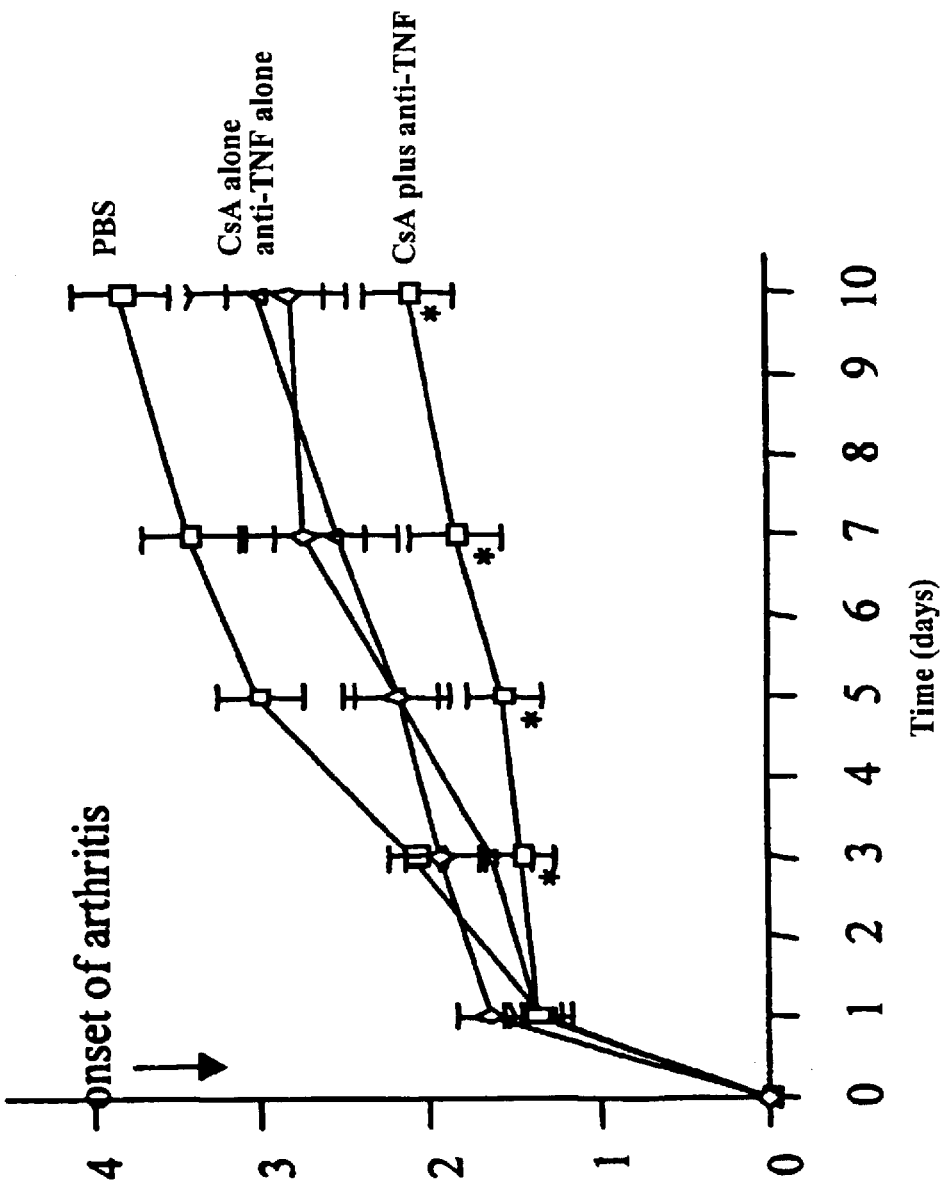
FIG. 5 is a graph showing the effect of administering 250 μg cyclosporin A alone, 50 μg anti-TNF antibody alone, and a combination of 250 μg cyclosporin A and 50 μg anti-TNF antibody to male DBA/1 mice on the suppression of arthritis as assessed by clinical score. Open square=control; triangle= cyclosporin A; diamond=anti-TNF antibody; square= cyclosporin A plus anti-TNF antibody. P<0.05 (vs. PBS treated group).

The results are presented in FIG. 5 and confirm that at sub-optimal doses neither CsA nor anti-TNF mAb, administered alone, significantly ameliorated disease. However, when the two reagents were given together, there was a highly significant reduction in the severity of arthritis. $P<0.05$ and relates to differences between the PBS treated group (Mann-Whitney U test). The results of this experiment show that there is an additive or synergistic ameliorative effect between CsA and anti-TNF antibody administered at sub-optimal doses.

Limb Involvement

In collagen-induced arthritis, as in RA, it is usual for additional limbs to become involved after the initial appearance of clinical disease and new limb involvement is an important indicator of the progression of the disease. To determine the effect of treatment with a sub-optimal dose of cyclosporin A in conjunction with a sub-optimal dose of anti-TNF mAb on new limb involvement, the number of limbs with clinically detectable arthritis at the end of the 10 day treatment period was compared with the number of limbs with arthritis before treatment. Results are shown in Table 10.

TABLE 10

Anti-CD4 Antibody and Cyclosporin A Prevent New Limb Recruitment

| Treatment | Limbs Affected (mean ± SEM) | | Increase (%) |
| --- | --- | --- | --- |
| | Day 1 | Day 10 | |
| Control mAb | 1.36 ± 0.20 | 2.45 ± 0.28 | 80.1% |
| Cyclosporin A | 1.36 ± 0.15 | 2.18 ± 0.30 | 60.3% |
| Anti-TNF mAb | 1.45 ± 0.16 | 1.9 ± 0.21 | 31.0% |
| CsA/Anti-TNF mab | 1.27 ± 0.14 | 1.54 ± 0.20[1] | 21.0% |

$P = 0.03$ (vs. control).

Treatment with a sub-optimal dose of cyclosporin A in conjunction with a sub-optimal dose of anti-TNF mAb resulted in statistically significant reductions in limb involvement in comparison to control monoclonal antibody ($P=0.03$).

Example 5

Treatment of Induced Arthritis in a Murine Model using Anti-TNF Antibody and a Sub-Optimal Dose of Cyclosporin A The murine model of collagen type II induced arthritis, described above, was used to investigate the ability of cyclosporin A to prolong the therapeutic effect of a single injection of anti-TNF antibody to modulate the severity of joint disease in collagen-induced arthritis. A comparison was made between the efficacy of treatment with a single injection of 300 μg anti-TNF antibody alone, and a combination of a single injection of 300 μg anti-TNF antibody and a sub-optimal dose of CsA.

Experimental Procedure

Male DBA/1 mice were immunized intradermally with 100 μg of bovine type II collagen emulsified in complete Freund's adjuvant (Difco Laboratories, East Molsey, UK). The mean day of onset of arthritis was approximately one month after immunization. After the onset of clinically evident arthritis (erythema and/or swelling in one or more limbs), three groups of mice (10 mice per group) were subjected to treatment with one of the following therapies: 250 μg (10 mg/kg) cyclosporin A (SANDIMMUNE®), Sandoz Pharmaceuticals, East Hanover, N.J.), injected intra-peritoneally in conjunction with 300 μg (12 mg/kg) L2 (the isotype control for anti-TNF antibody), injected intra-peritoneally, on day one; 250 μg cyclosporin A, injected intra-peritoneally in conjunction with 300 μg (12 mg/kg) anti-TNF mAb, injected intra-peritoneally, on day one; or 300 μg anti-TNF mAb TN3-19.12, injected intra-peritoneally on day one. Arthritis was monitored for paw swelling (measured with calipers) for 10 days, after which the mice were sacrificed and joints were processed for histology.

paw-Swelling

Figure 6:
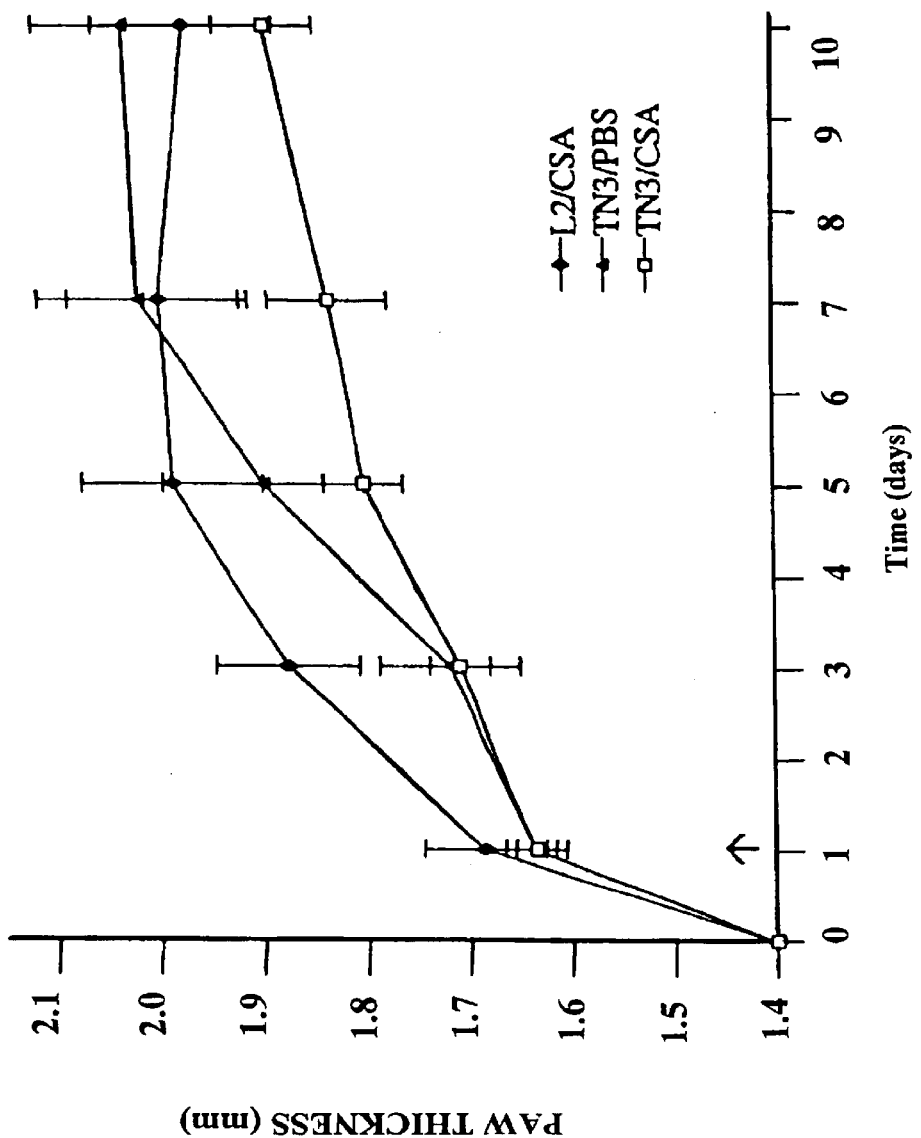
FIG. 6 is a graph showing the effect of administering 300 μg anti-TNF antibody alone, a combination of 250 μg cyclosporin A and 300 μg control antibody L2, and a combination of 250 μg cyclosporin A and 300 μg anti-TNF antibody to male DBA/1 mice on the suppression of arthritis as assessed by paw-swelling measurements. Open square= cyclosporin A plus anti-TNF antibody; diamond= cyclosporin A plus control antibody; triangle=anti-TNF antibody.

Paw-swelling was monitored as described in Example 4. Treatment with a sub-optimal dose of cyclosporin A in conjunction with a single injection of anti-TNF mAb (300 μg) resulted in a sustained reduction in paw-swelling over the treatment period, relative to mice treated with a sub-optimal dose of CsA in conjunction with the control antibody and mice treated with 300 μg anti-TNF mAb alone. Results are shown in FIG. 6.

Histology

Sagittal sections of the PIP joint of the middle digit of each mouse (from the first paw with clinical arthritis) were examined in a blind fashion by microscopy and classified according to the presence or absence of erosions, using the procedure described in Example 1. Comparisons were thus made between identical joints, and the arthritis was of equal duration. Results are shown in Table 11.

TABLE 11

PIP Joint Erosions

| Treatment | Incidence of Erosions |
|---|---|
| L2/CsA | 8/10 (80%) |
| TN3 alone | 8/9 (89%) |
| CsA/TN3 | 6/10 (60%) |

In mice given a sub-optimal dose of CsA in conjunction with 300 μg of anti-TNF mAb, the proportion of joints showing erosive changes was reduced to 60% whereas, in the group of mice given a sub-optimal dose of CsA plus control antibody, 80% of the joints were eroded, and in the group of mice given 300 μg anti-TNF mAb, 89% of the joints were eroded. Thus, treatment with a sub-optimal dose of CsA in conjunction with 300 μg anti-TNF mAb provided a degree of protection against joint erosion.

Example 6

Treatment of Induced Arthritis in a Murine Model Using Cyclosporin A and Anti-TNF Antibody at Effective Doses Using the murine model of collagen type II induced arthritis, described above, a comparison was made between the efficacy of treatment with CsA alone, anti-TNF antibody alone, and a combination of CsA and anti-TNF antibody, for the ability to modulate the severity of joint disease in collagen-induced arthritis.

Experimental Procedure

Male DBA/1 mice were immunized intradermally with 100 μg of bovine type II collagen emulsified in complete Freund's adjuvant (Difco Laboratories, East Molsey, UK). The mean day of onset of arthritis was approximately one month after immunization. After the onset of clinically evident arthritis (erythema and/or swelling in one or more limbs), three groups of mice (11–12 mice per group) were subjected to treatment with one of the following therapies: 500 μg (20 mg/kg) cyclosporin A (SANDIMMUNE®, Sandoz Pharmaceuticals, East Hanover, N.J.), injected intra-peritoneally daily; 250 μg (10 mg/kg) anti-TNF mAb TN3-19.12, injected intra-peritoneally once every three days (days 1, 4 and 7); or 500 μg cyclosporin A, injected intra-peritoneally daily in conjunction with 250 μg anti-TNF mAb, injected intra-peritoneally once every three days. A control group of 24 mice was administered PBS, injected intra-peritoneally daily, after the onset of clinically evident arthritis. Arthritis was monitored for paw swelling (measured with calipers) for 10 days, after which the mice were sacrificed and joints were processed for histology.

Clinical Score

Clinical score was assessed on the following scale: 0=normal; 1=slight swelling and/or erythema; 2=pronounced edematous swelling; and 3=joint rigidity. Each limb was graded, giving a maximum score of 12 per mouse.

Figure 7:
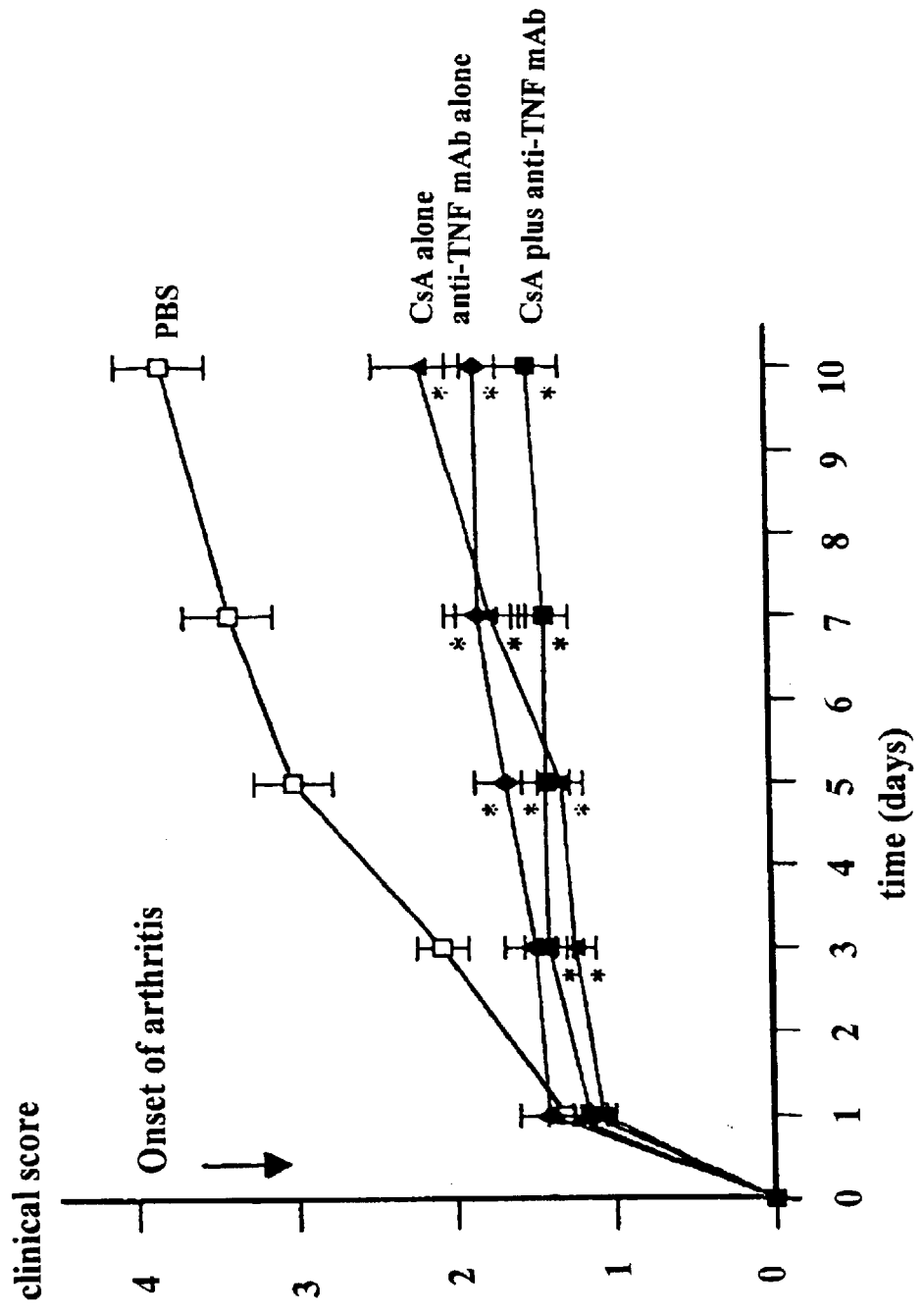
FIG. 7 is a graph showing the effect of administering 500 μg cyclosporin A alone, 250 μg anti-TNF antibody alone, and a combination of 500 μg cyclosporin A and 250 μg anti-TNF antibody to male DBA/1 mice on the suppression of arthritis as assessed by clinical score. Open square= control; diamond=anti-TNF antibody; triangle=cyclosporin A; square=cyclosporin A plus anti-TNF antibody. P<0.05 (vs. PBS treated group).

The results are presented in FIG. 7 and show that treatment with 500 μg cyclosporin A plus 250 μg anti-TNF mAb resulted in a significant reduction in the severity of arthritis over the treatment period, relative to the control group (PBS treated group). Treatment with either 250 μg anti-TNF mAb alone or 500 μg cyclosporin A alone also reduced the severity of arthritis. (P<0.05 and relates to differences between the PBS treated group (Mann-Whitney U test)).

Histology

For histology, the mice were sacrificed after 10 days and the first limb that had shown clinical evidence of arthritis was removed from each mouse, formalin-fixed, decalcified, and wax-embedded before sectioning and staining with haematoxylon and eosin. A sagittal section of the proximal interphalangeal (PIP) joint of the middle digit was examined by microscopy in a blind fashion for the presence or absence of erosions in either cartilage or bone (defined as demarcated defects in cartilage or bone filled with inflammatory tissue). Comparisons were made between the same joints, and the arthritis was of identical duration. Erosions were observed in 9% of the PIP joints from the group of mice treated with a combination of 500 μg (20 mg/kg) CsA and 250 μg (10 mg/kg) anti-TNF mAb compared with in 36% of the PIP joints from the group of mice treated with 500 μg CsA alone and 42% of the PIP joints from the group of mice treated with 250 μg anti-TNF antibody alone. The results of the experiment are shown in Table 13.

TABLE 13

Therapeutic Effects of Cyclosporin A and Anti-TNF Monoclonal Antibody in Established Collagen-Induced Arthritis

| Treatment | No. mice per group | Histology: proportion of PIP joints with erosions |
|---|---|---|
| PBS | 24 | 23/24 (96%) |
| CsA (20 mg/kg) | 12 | 4/11 (36%) (P < 0.001) |
| Anti-TNF mAb (10 mg/kg) | 12 | 5/12 (42%) (P < 0.001) |
| CsA (20 mg/kg) plus anti-TNF mAb (10 mg/kg) | 11 | 1/10 (9%) (P < 0.001) |

P values refer to comparisons with the PBS-treated group.

P values refer to comparisons with the PBS-treated group.

Treatment with cyclosporin A in conjunction with anti-TNF antibody provides a greater degree of protection against arthritis than treatment with either reagent alone. The results show that there is an additive or synergistic ameliorative effect between cyclosporin A and anti-TNF antibody.

Example 7

Treatment of Induced Arthritis in a Murine Model Using Rolipram and Anti-CD4 Antibody The murine model of collagen type II induced arthritis, described above, was used to investigate the efficacy of the TNF antagonist rolipram in conjunction with anti-TNF monoclonal antibody or anti-CD4 monoclonal antibody, for the ability to modulate the severity of joint disease in collagen-induced arthritis. First, a comparison was made between the efficacy of rolipram treatment and anti-TNF monoclonal antibody (mAb) treatment. Second, therapy with rolipram in conjunction with anti-TNF mAb was investigated. Third, therapy with rolipram in conjunction with anti-CD4 mAb was investigated. Rolipram is a type IV phosphodiesterase (PDE IV) inhibitor that has been reported to suppress TNFα production via a cyclic 3',5'-adenosine monophosphate (cAMP) dependent mechanism.

A. Experimental Procedure

Male DBA/1 mice were immunized intradermally with 100 μg of bovine type II collagen emulsified in complete Freund's adjuvant (Difco Laboratories, East Molsey, UK). The mean day of onset of arthritis was approximately one month after immunization. After the onset of clinically evident arthritis (erythema and/or swelling in one or more limbs), mice were injected intra-peritoneally with therapeutic agents. Arthritis was monitored for clinical score and paw swelling (measured with calipers) for 10 days. The therapeutic agents included rolipram, anti-TNF antibody, and anti-CD4 antibody.

B. Comparison of Treatment with Rolipram or Anti-TNF Antibody

Using the Experimental Procedure described above, three groups of mice (6 mice per group) were subjected to treatment with one of the following therapies: Cremophor EL® (control; Sigma), injected intra-peritoneally twice daily; either 3 mg/kg body weight, 5 mg/kg body weight or 10 mg/kg body weight of rolipram (Schering A. G.; Berlin, Germany) dissolved in Cremophor EL®, injected intra-peritoneally twice daily; or 300 μg (12 mg/kg) anti-TNF antibody TN3-19.12, injected intra-peritoneally once every three days (days 1, 4 and 7).

Clinical Score

Clinical Score was assessed on the following scale: 0=normal; 1=slight swelling and/or erythema; 2=pronounced edematous swelling; and 3=joint rigidity. Each limb was graded, giving a maximum score of 12 per mouse.

Figure 8:
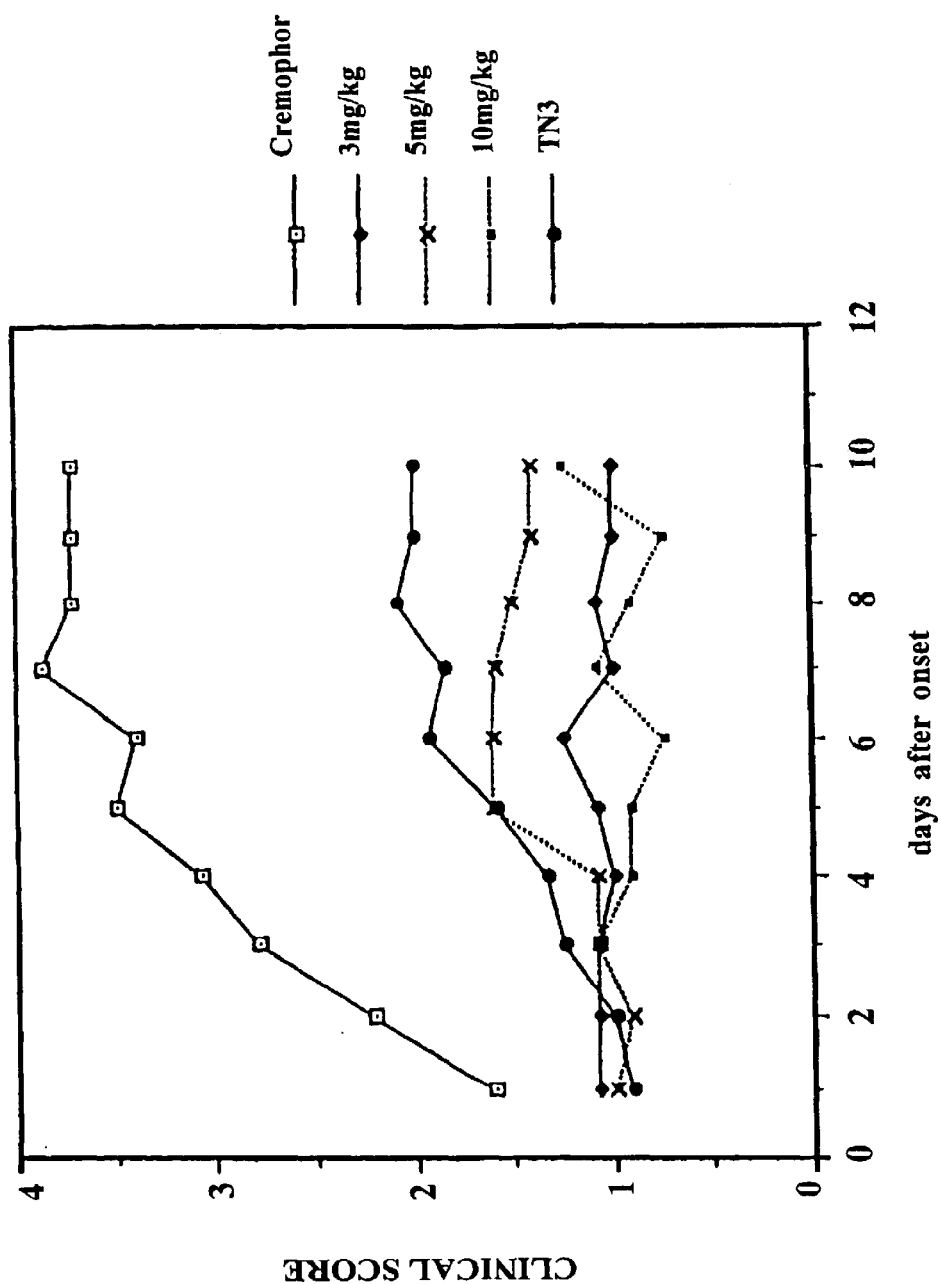
FIG. 8 is a graph comparing the effects of administering Cremophor EL® (negative control) alone, either 3 mg/kg, 5 mg/kg or 10 mg/kg of rolipram alone, and 300 μg anti-TNF antibody alone to male DBA/1 mice on the suppression of arthritis as assessed by clinical score. Square with black dot=negative control; diamond=3 mg/kg rolipram; x=rolipram (5 mg/kg); square=rolipram (10 mg/kg); circle= anti-TNF antibody.

The results are presented in FIG. 8 and show that treatment with rolipram resulted in a significant reduction in the severity of arthritis over the treatment period, relative to mice treated with Cremophor EL®. For example, the mean clinical score on day 10 (±SE) was 1.0±0.3 for mice treated with 3 mg/kg rolipram ($P<0.05$ (vs. control)), 2.0±0.4 for mice treated with anti-TNF mAb, and 3.7±0.7 for mice treated with Cremophor EL® (control arthritic mice), indicating that the magnitude of the therapeutic effect of rolipram treatment was comparable to, or greater than anti-TNF antibody treatment. Preliminary immunohistochemical studies designed to elucidate the mechanism by which rolipram ameliorates disease in this murine model of collagen type II induced arthritis suggest that rolipram treatment results in down-regulation of TNF expression in the joints of mice with collagen-induced arthritis. These findings indicate that rolipram is effective in established collagen-induced arthritis and may therefore be useful in the treatment of RA.

C. Effect of Treatment with Rolipram in Conjunction with Anti-TNF Antibody

Using the Experimental Procedure described above, 10 mice were subjected to treatment with one of the following therapies: Cremophor EL® (control), injected intra-peritoneally twice daily; rolipram (either 0.5 mg/kg body weight, 3 mg/kg body weight or 5 mg/kg body weight) dissolved in Cremophor EL®, injected intra-peritoneally twice daily; 300 μg (12 mg/kg) anti-TNF antibody TN3-19.12, injected intra-peritoneally once every three days (days 1, 4 and 7); or 300 μg anti-TNF antibody TN3-19.12, injected intra-peritoneally once every three days, in conjunction with rolipram (5 mg/kg body weight) dissolved in Cremophor EL®, injected intra-peritoneally twice daily.

Clinical Score

Clinical Score was assessed on the following scale: 0=normal; 1=slight swelling and/or erythema; 2=pronounced edematous swelling; and 3=joint rigidity. Each limb was graded, giving a maximum score of 12 per mouse.

Figure 9:
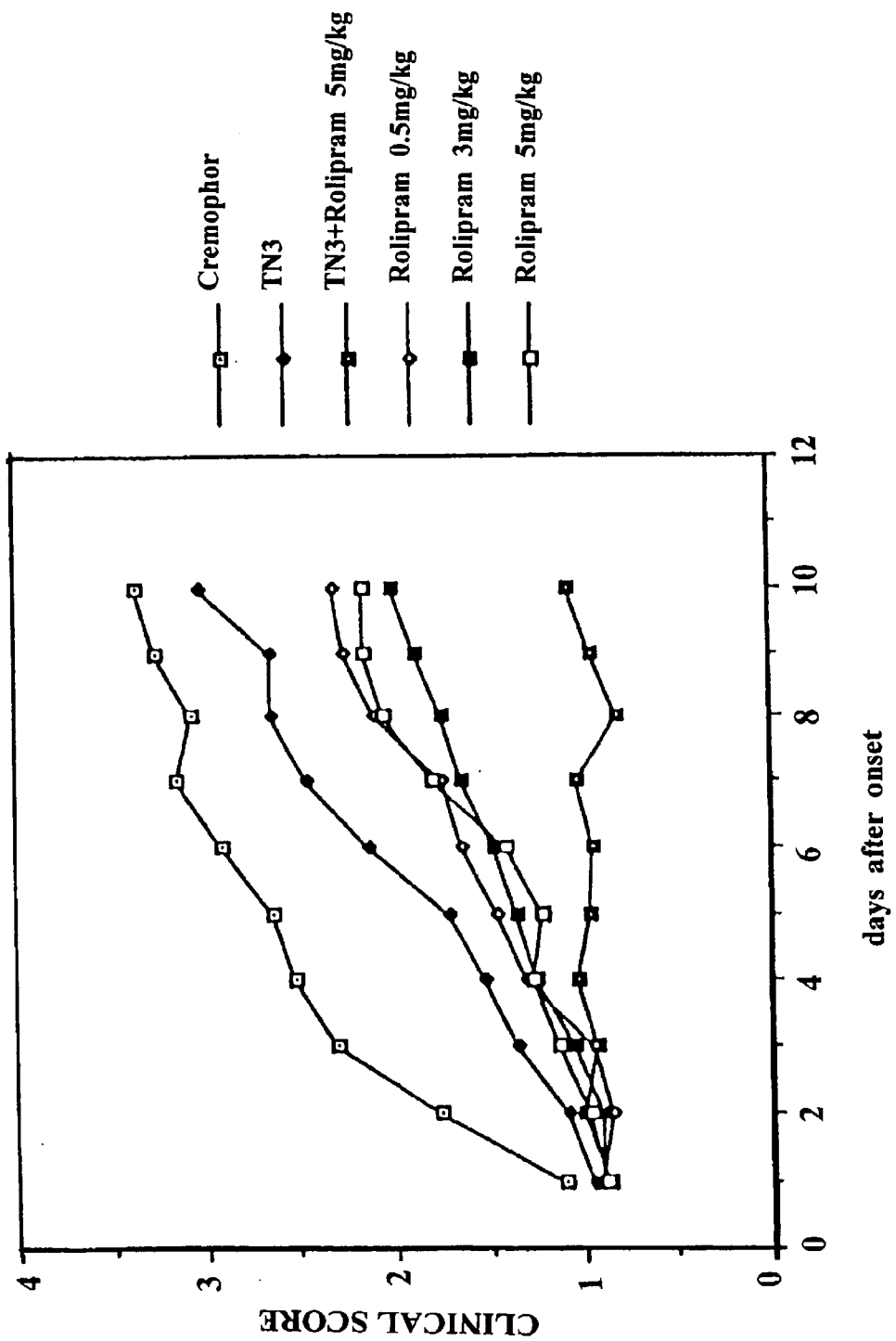
FIG. 9 is a graph showing the effect of administering Cremophor EL® (negative control) alone, either 0.5 mg/kg, 3 mg/kg or 5 mg/kg of rolipram alone, 300 μg anti-TNF antibody alone, and a combination of 5 mg/kg rolipram and 300 μg anti-TNF antibody to male DBA/1 mice on the suppression of arthritis as assessed by clinical score. Square with black dot=negative control; diamond=anti-TNF antibody; square with white dot=rolipram plus anti-TNF antibody; diamond with white dot=rolipram (0.5 mg/kg); square=rolipram (3 mg/kg); open square=rolipram (5 mg/kg).

The results are presented in FIG. 9 and show that co-administration of, for example, two different TNF antagonists provides a more complete therapeutic effect than administration of either antagonist alone in modulating the severity of joint disease in collagen-induced arthritis. This suggests that there is an additive or synergistic ameliorative effect between different TNF antagonists.

D. Effect of Treatment with Rolipram in Conjunction with Anti-CD4 Antibody

Using the Experimental Procedure described above, 9 mice were subjected to treatment with one of the following therapies: Cremophor EL®, injected intra-peritoneally twice daily; rolipram (5 mg/kg body weight) dissolved in Cremophor EL®, injected intra-peritoneally twice daily; 50 μg anti-CD4 antibody (rat IgG2b) (1:1 mixture of YTS 191.1.2 and YTA 3.1.2), injected intra-peritoneally once every three days (days 1, 4 and 7); or 50 μg anti-CD4 antibody, injected intra-peritoneally once every three days, in conjunction with rolipram (5 mg/kg body weight) dissolved in Cremophor EL®, injected intra-peritoneally twice daily.

Clinical Score

Clinical Score was assessed on the following scale: 0=normal; 1=slight swelling and/or erythema; 2=pronounced edematous swelling; and 3=joint rigidity. Each limb was graded, giving a maximum score of 12 per mouse.

Figure 10A:
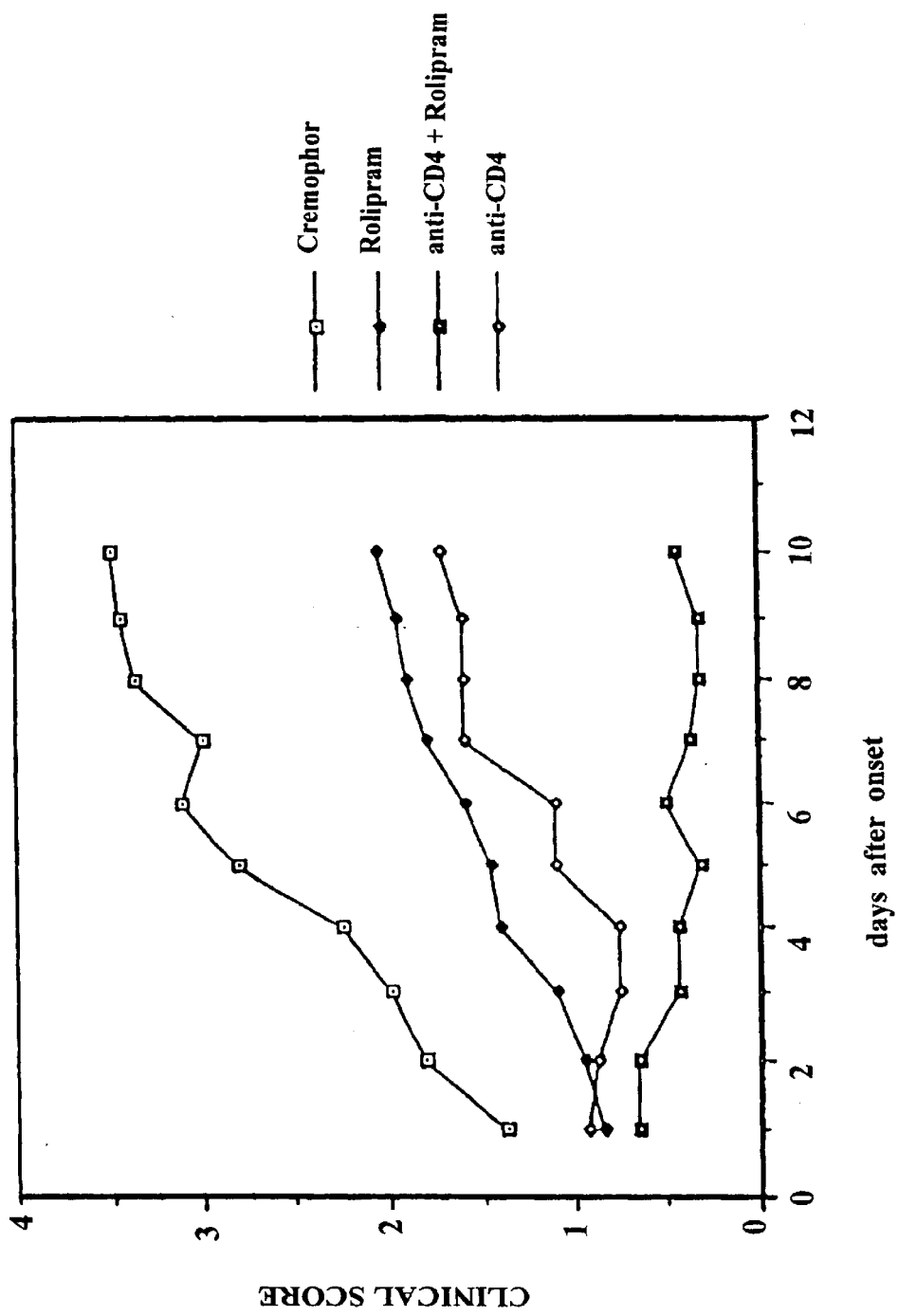

The results are presented in FIG. 10A and show that when rolipram and anti-CD4 antibody were co-administered, there was a highly significant reduction in the severity of arthritis over the treatment period. The results of this experiment show that there is an additive or synergistic ameliorative effect between rolipram and anti-CD4 antibody.

Paw-Swelling

Paw-swelling was monitored throughout the treatment period by measuring the thickness of each affected hind paw with calipers. The results are expressed as paw thickness (mm).

Treatment with rolipram in conjunction with anti-CD4 mAb resulted in a significant reduction in paw-swelling over the treatment period, relative to mice treated with rolipram alone or mice treated with anti-CD4 mAb alone. Results are shown in FIG. 10B. The results of this experiment show that there is an additive or synergistic ameliorative effect between rolipram and anti-CD4 antibody.

Equivalents

While this invention has been particularly shown and described with references to preferred embodiments thereof, it will be understood by those skilled in the art that various changes in form and details may be made therein without departing from the spirit and scope of the invention as defined by the appended claims.

What is claimed is:

1. A method of treating rheumatoid arthritis in an individual in need thereof comprising administering to the individual cyclosporin in combination with an anti-tumor necrosis factor alpha antibody or antigen-binding fragment thereof, in therapeutically effective amounts, wherein neither the dose of cyclosporin nor the dose of anti-tumor necrosis factor alpha antibody or antigen-binding fragment thereof alone would have any significant effect on the severity of rheumatoid arthritis in the individual.

2. A method of claim 1 wherein the antibody or fragment is a chimeric antibody or chimeric fragment, wherein said chimeric antibody or chimeric fragment comprises a non-human variable region specific for TNFα or an antigen-binding fragment thereof and a human constant region.

* * * * *